(12) United States Patent
Contijoch et al.

(10) Patent No.: US 11,986,337 B2
(45) Date of Patent: May 21, 2024

(54) DOSE REDUCTION FOR CARDIAC COMPUTED TOMOGRAPHY

(71) Applicant: The Regents of the University of California, Oakland, CA (US)

(72) Inventors: Francisco Contijoch, La Jolla, CA (US); Brendan Colvert, La Jolla, CA (US); Elliot McVeigh, La Jolla, CA (US)

( * ) Notice: Subject to any disclaimer, the term of this patent is extended or adjusted under 35 U.S.C. 154(b) by 38 days.

(21) Appl. No.: 17/375,895

(22) Filed: Jul. 14, 2021

(65) Prior Publication Data
US 2022/0022836 A1 Jan. 27, 2022

Related U.S. Application Data

(60) Provisional application No. 63/219,337, filed on Jul. 7, 2021, provisional application No. 63/051,782, filed on Jul. 14, 2020.

(51) Int. Cl.
*A61B 6/00* (2006.01)
*A61B 6/03* (2006.01)
(Continued)

(52) U.S. Cl.
CPC .............. *A61B 6/542* (2013.01); *A61B 6/032* (2013.01); *A61B 6/4035* (2013.01); *A61B 6/503* (2013.01);
(Continued)

(58) Field of Classification Search
CPC .. H05G 1/30; H05G 1/36; H05G 1/02; H05G 1/44; H05G 1/60; A61B 6/4035; A61B 6/503; A61B 6/542; A61B 6/032; A61B 6/107; A61B 6/5205; A61B 6/037; A61B 6/025; A61B 6/4233; A61B 6/4007; A61B 6/583; A61B 6/4085; A61B 6/484; A61B 6/50; A61B 6/582; A61B 6/5217; A61B 6/465; A61B 6/4014; A61B 6/4435; A61B 6/4476; A61B 6/4488; A61B 6/481; A61B 6/488; A61B 6/54; A61B 6/06; A61B 6/545; A61B 6/544; A61B 6/00; A61B 6/40; A61B 6/4441; A61B 6/469; A61B 6/482; A61B 6/405; A61B 6/035; A61B 6/0435; A61B 6/4078; A61B 6/502; A61B 6/5294; A61B 6/5258; A61B 6/5282; A61B 6/12; A61B 6/486; A61B 6/501;
(Continued)

(56) References Cited

U.S. PATENT DOCUMENTS 7,630,477 B2 12/2009 Toth et al.
11,083,428 B2 * 8/2021 Tsukagoshi ............ A61B 6/488
(Continued)

OTHER PUBLICATIONS

Mettler, F.A. et al., "CT scanning: patterns of use and dose," J Radiol. Protection, vol. 20, pp. 353-359, 1991.
(Continued)

*Primary Examiner* — Irakli Kiknadze
(74) *Attorney, Agent, or Firm* — Perkins Coie LLP

(57) ABSTRACT

Methods, devices, and systems for computed tomography (CT) imaging technologies that are tailored to specific regions of interest and provide a reduced radiation dose. An imaging system for cardiac CT comprises a beam-shaping filtration and exposure control technologies specifically tailored to imaging of the heart.

20 Claims, 23 Drawing Sheets

(51) Int. Cl.
  A61B 6/40    (2024.01)
  A61B 6/50    (2024.01)
  G16H 10/60   (2018.01)
  G16H 20/40   (2018.01)
  H05G 1/30    (2006.01)
(52) U.S. Cl.
  CPC .............. *G16H 10/60* (2018.01); *G16H 20/40* (2018.01); *H05G 1/30* (2013.01)
(58) Field of Classification Search
  CPC ........ A61B 6/027; G16H 30/40; G16H 40/67; G16H 20/40; G16H 30/20; G16H 50/50; G16H 50/20; G16H 10/60; G16H 20/10; G16H 40/63; G21K 1/10; G21K 1/04; G21K 1/046; G21K 1/02; G21K 1/025; G01T 1/2985; G01T 1/2992; G01T 1/167; G01T 1/2018; G06T 11/006; G06T 11/008; G06T 5/002; G06T 11/005; G06T 7/11; G06T 7/0014; G06T 2211/424; G06T 2211/432; G06K 9/6256; G06N 3/02; G06F 19/00; G02B 5/201; G02B 26/023
  USPC .......................................... 378/4, 16, 19, 62
  See application file for complete search history.

(56) References Cited

U.S. PATENT DOCUMENTS

| | | | | |
|---|---|---|---|---|
| 2004/0234037 | A1* | 11/2004 | Hoffman | A61B 6/032 378/156 |
| 2011/0033030 | A1* | 2/2011 | Loos | G21K 1/10 378/156 |
| 2011/0091017 | A1* | 4/2011 | Friedlander | H05G 1/265 378/146 |
| 2013/0058451 | A1* | 3/2013 | Hsieh | A61B 6/542 378/16 |
| 2014/0328453 | A1* | 11/2014 | Hsieh | A61B 6/405 378/16 |
| 2015/0313569 | A1* | 11/2015 | Stevens | A61B 6/544 378/8 |
| 2018/0317867 | A1* | 11/2018 | Boone | A61B 6/0435 |
| 2019/0029622 | A1* | 1/2019 | Tamura | A61B 6/4241 |
| 2019/0336086 | A1* | 11/2019 | Proksa | A61B 6/4035 |
| 2020/0330065 | A1* | 10/2020 | Zhan | A61B 6/4035 |
| 2021/0045703 | A1* | 2/2021 | Crotty | A61B 6/542 |
| 2021/0361253 | A1* | 11/2021 | Griffiths | A61B 6/581 |

OTHER PUBLICATIONS

Ding, A. et al., "Virtual Dose: A software for reporting organ doses from CT for adult and pediatric patients," Physics in Medicine and Biology, vol. 60, No. 14, pp. 5601-5625, 2015.
Brenner D.J. et al., "Computed Tomography—An Increasing Source of Radiation Exposure," New England Journal of Medicine, vol. 357, No. 22, pp. 2277-2284, 2007.
Smith-Bindman, R., "Is Computed Tomography Safe?" New England Journal of Medicine, pp. 2010-2013, 2010.
Halliburton, S. et al., "SCCT guidelines on radiation dose and dose-optimization strategies in cardiovascular CT," Yearbook of Diagnostic Radiology, vol. 2012, p. 233, 2012.
Greenland, P. et al., "Coronary Artery Calcium Score Combined With Framingham Score for Risk Prediction in Asymptomatic Individuals," Journal of the American Medical Association, vol. 291, No. 2, pp. 210-215, 2004.
McCollough, C.H. et al., "Coronary artery calcium: a multi-institutional, multimanufacturer international standard for quantification at cardiac CT," Radiology, vol. 243, No. 2, pp. 527-538, 2007.
Miller, J.M. et al., "Diagnostic Performance of Coronary Angiography by 64-Row CT," New England Journal of Medicine, vol. 359, No. 22, pp. 2324-2336, 2008.
Hausleiter, J. et al., "Estimated radiation dose associated with cardiac CT angiography," Journal of the American Medical Association, vol. 301, No. 5, pp. 500-507, 2009.
Clackdoyle, R. et al., "Tomographic Reconstruction in the 21$^{st}$ Century," IEEE Signal Processing Magazine, vol. 27, No. 4, pp. 60-80, 2010.
Wang, G. et al., "Meaning of Interior Tomography," Physics in Medicine and Biology, vol. 58, No. 16, p. R161, 2013.
Bartolac, S. et al., "Fluence field optimization for noise and dose objectives in CT," Medical Physics, vol. 38, No. SUPPL.1, 2011, pp. S1-S16.
Hsieh, S.S. et al., "The feasibility of a piecewise-linear dynamic bowtie filter The feasibility of a piecewise-linear dynamic bowtie filter," vol. 031910, No. 2013, pp. 1-12, 2015.
Szczykutowicz, T.P. et al., "Fluid dynamic bowtie attenuators," Medical Imaging 2015: Physics of Medical Imaging, vol. 9412, No. Mar. 2015, p. 94120X, 2015.
Stayman, J.W., et al., "Fluence-Field Modulated X-ray CT using Multiple Aperature Devices," vol. 118, No. 24, pp. 6072-6078, 2016.
Wang, W., et al., "Volume-of-interest CT imaging with dynamic beam filtering using multiple aperture devices," Proceedings of the International Conference on Image Formation in X-ray Computed Tomography, pp. 213-217, 2018.
Hubbell, J., et al., "Tables of X-Ray Mass Attenuation Coefficients and Mass-Energy Absorption Coefficients from 1 keV to 20 MeV for Elements Z=1 to 92 and 48 Additional Substances of Dosimetric Interest," 2004, 120 pages.
Contijoch, F. et al., "The impact of small motion on the visualization of coronary vessels and lesions in cardiac CT: A simulation study: A," Medical Physics, vol. 44, No. 7, pp. 3512-3524, 2017.
Kak, A.C., et al., "5 Aliasing Artifacts and Noise in CT images BT," Principles of Computerized Tomographic Imaging, 2002, 177-201.
Joseph P.M., et al., "View sampling requirements in fan beam computed tomography," Medical Physics, vol. 7, No. 6, pp. 692-702, 1980.
Mail, N. et al., "The Influence of Bowtie Filtration On Cone-Beam CT Image Quality," Medical Physics, vol. 36, No. 1, pp. 22-32, 2009.
Natterer, F. et al., "Mathematical Methods in Image Reconstruction," SIAM, 2001, 224 pages.
Cho Z.H. et al., "Limited Field of View Reconstruction=Eo," Sciences-New York, No. 1, pp. 546-551, 1979.
Wagner, W., et al., "Reconstructions from Restricted Region Scan Data—New Means to Reduce the Patient Dose," No. 2, pp. 2866-2869, 1979.
Louis A.K. et al., "Mathematical problems of computerized tomography," Proc. IEEE, vol. 71, No. 3, pp. 379-389, 1983.
Srinivasa, N. et al., "Image reconstruction from truncated projections: A linear prediction approach," pp. 1733-1736, 2005.
Ohnesorge, B., et al., "Efficient correction for CT image artifacts caused by objects extending outside the scan field of view," Medical Physics, vol. 27, No. 1, pp. 39-46, 2002.
Van Gompel, G. et al., "A new algorithm for 2D region of interest tomography," Medical Imaging 2004: Image Processing, vol. 5370, No. May, p. 2105, 2004.
Soderberg, M. et al., "Automatic exposure control in computed tomography an evaluation of systems from different manufacturers," Acta Radiologica, vol. 51, No. 6, pp. 625-634, 2010.
Mccollough, C.H. et al., "CT Dose Reduction and Dose Management Tools: Overview of Available Options," pp. 503-513, 2006.
Bruesewitz, M.R. et al., "Smart mA-Automatic Exposure Control (AEC): Physics Principles and Practical Hints," Tech. Rep., 2008, 1 page.
Wang, M.C. et al., "Using the Normal Quantile Plot to Explore Meta-Analytic Data Sets," Psychological Methods, vol. 3, No. 1, pp. 46-54, 1998.
Imai, K. et al., "Statistical characteristics of streak artifacts on CT images: Relationship between streak artifacts and mA s values," Medical Physics, vol. 36, No. 2, pp. 492-499, 2009.

(56) References Cited

OTHER PUBLICATIONS

Jin, P. et al., "A Model-Based Image Reconstruction Algorithm with Simultaneous Beam Hardening Correction for X-Ray CT," IEEE Transactions on Computational Imaging, vol. 1, No. 3, pp. 200-216, 2015.

\* cited by examiner

DOSE REDUCTION FOR CARDIAC COMPUTED TOMOGRAPHY

RELATED APPLICATIONS

This patent document claims priority to and the benefits of U.S. Provisional Patent Application No. 63/051,782, titled "DOSE REDUCTION FOR CARDIAC COMPUTED TOMOGRAPHY", filed on Jul. 14, 2020. This patent document further claims priority to and the benefits of U.S. Provisional Patent Application No. 63/219,337, titled "CARDIAC REGION OF INTEREST PREDICTION", filed on Jul. 7, 2021. The entire contents of the above-noted provisional applications are incorporated by reference as part of the disclosure of this patent document.

STATEMENT REGARDING FEDERALLY SPONSORED RESEARCH OR DEVELOPMENT

This invention was made with government support under HL144678, HL143113 and HL116395 awarded by the National Institutes of Health. The government has certain rights in the invention.

TECHNICAL FIELD

The subject matter of this patent document relates generally to computed tomography (CT) imaging, and in particular to methods and apparatus for reducing radiation dose in X-ray CT imaging.

BACKGROUND

X-ray computed tomography (CT) is a powerful medical imaging modality with many clinical applications including screening for disease, diagnosis, and preprocedural planning. CT scanners typically use an X-ray tube and an array of detectors placed opposite to the X-ray tube in a rotating gantry to measure X-ray attenuation by different tissues inside a body. Multiple X-ray measurements taken from different angles are processed using reconstruction algorithms to produce cross-sectional (tomographic) images of the body.

SUMMARY OF CERTAIN EMBODIMENTS

The techniques disclosed herein can be implemented in various embodiments to implement methods and apparatus that significantly reduce radiation dose in X-ray computed tomography.

An aspect of the disclosed embodiments relates to a method of reducing radiation dose in computed tomography (CT) imaging that includes positioning a region of interest of an imaging target proximate to an isocenter of a CT scanner. The method further includes adjusting a fluence of X-ray radiation produced by an X-ray source of the CT scanner using a beam-shaping filter, wherein the beam-shaping filter is disposed between the X-ray source of the CT scanner and the region of interest, and wherein the beam-shaping filter is configured to attenuate the X-ray radiation on areas of the imaging target located outside of the region of interest and simultaneously transmit the X-ray radiation to the areas of the imaging target located outside of the region of interest to provide a fluence of the X-ray radiation on the areas of the imaging target located outside of the region of interest at a level less than a predetermined fraction of a fluence of the X-ray radiation within the region of interest.

Another aspect of the disclosed technology relates to a computed tomography (CT) scanner that includes an X-ray source and a beam-shaping filter disposed between the X-ray source and a location where a region of interest of an imaging target is placed. The CT scanner is configured such that an isocenter of the CT scanner is proximate to the region of interest. The CT scanner is further configured to adjust a fluence of X-ray radiation produced by the X-ray source using the beam-shaping filter, wherein the beam-shaping filter is configured to attenuate the X-ray radiation on areas of the imaging target located outside of the region of interest and, at the same time, transmit the X-ray radiation to the areas of the imaging target located outside of the region of interest to provide a fluence of the X-ray radiation on the areas of the imaging target located outside of the region of interest at a level less than a predetermined fraction of a fluence of the X-ray radiation within the region of interest.

DETAILED DESCRIPTION

Figure 1A:
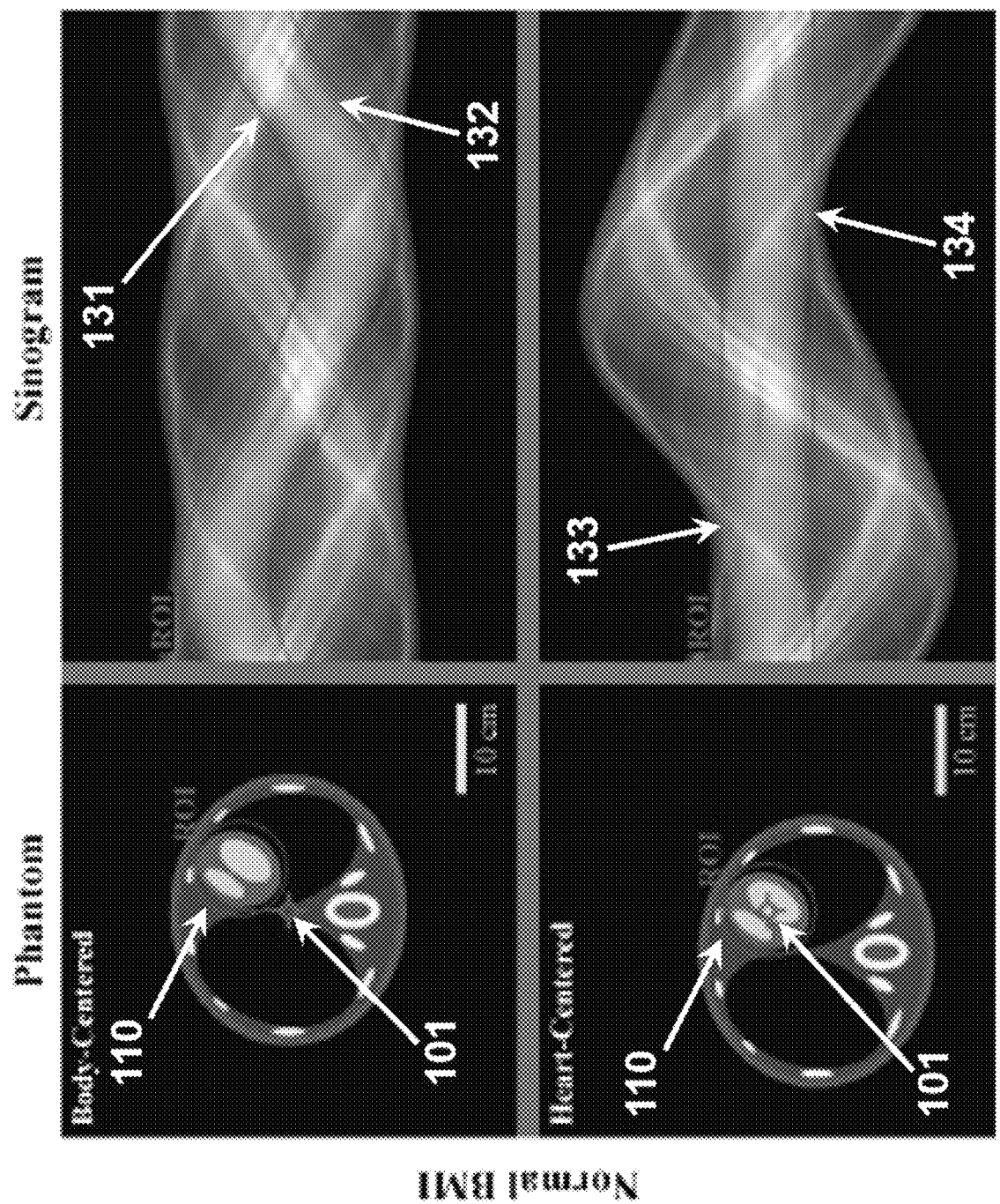
FIG. 1A shows an anthropomorphic digital phantom for a normal person representing an axial slice of the person's chest cavity.

Despite the many clinical benefits afforded by CT imaging, the use of ionizing radiation and the steady increase in the number of CT scans per capita have raised concerns about increased accumulation of radiation dose in the population. Under federal regulations, radiation dose from CT imaging should be as low as reasonably achievable, known as "ALARA." To allay the radiation dose concerns, acquisition technologies have been developed to specify a variety of parameters including beam-shaping filtration, tube current and voltage, and reconstruction methods, which are tuned to reduce delivered dose and provide sufficient image quality for various clinical tasks.

Conventional imaging requires the entire object within the field of view to be irradiated with X-rays to allow for accurate image reconstruction. Decreasing the spatial extent of the X-ray beam can lead to the interior tomography problem. While filters have been proposed to shape the beam in new ways, those filters are modulated dynamically which adds complexity and requires a redesign of the X-ray system. Technology disclosed in this patent document enables a way to reduce X-ray dose for the patient without encountering the interior tomography problem. Specifically, a static X-ray beam filter can be used. The interior tomography problem arises when a region of interest (ROI) of an imaging target is irradiated with X-rays only through the ROI to recover the ROI image. The technology disclosed herein alleviates the interior tomography problem through the disclosed features that include the use of a static X-ray beam-shaping filter that provides the highest fluence of the X-ray radiation from an X-ray source of a CT scanner in the ROI and simultaneously maintains a level of fluence on the areas of the imaging target located outside the ROI at a level above a certain predetermined threshold value. The fact that the fluence in such approach is nonzero outside the ROI effectively prevents local tomography artifacts through obtaining noisy projection information about the entire imaging target permitting conventional reconstruction.

In addition, according to certain implementations of the disclosed technology, the X-ray tube current can be modulated as a function of gantry position to account for dependence of attenuation of X-rays passing through the region of interest on the view angle. Traditional implementations assume that an object has homogenous attenuation properties and are not tailored for optimal imaging of a specific region of interest. By tailoring the X-ray tube current modulation to the optimal values for the region of interest, image quality can be improved by decreasing the level of the image noise within the region of interest. Information about the attenuation of X-rays passing through the region of interest can be obtained, for example, using low-dose CT projection radiographs (scouts).

Methods according to the disclosed technology allow specifying (or estimating) position of a region of interest (e.g., heart) within a body without performing any imaging scans. In some example embodiments, the ROI position can be determined based on such characteristics of a person as, for example, age, sex, body mass index (BMI), race, ethnicity. The location and size of a ROI (e.g., heart) can also be obtained by methods and devices according to the disclosed technology using information from CT scans (e.g., scout scans).

Methods according to the disclosed technology allow predicting the location of the heart for tailored imaging using patient's demographic information. Therefore, methods according to the disclosed technology enable improved CT imaging (e.g., allowing for reduced dose) and can be extended to other cardiac CT applications as well as non-CT applications such as nuclear medicine imaging and MRI.

Methods according to the disclosed technology also allow predicting the location of each coronary vessel separately which enables even more tailored evaluation if only one vessel is of interest.

When imaging a patient's heart, the subject is typically centered in the scanner according to their chest cavity dimensions. This is suboptimal for heart imaging as the heart is off-center (anterior and lateral) and represents a smaller region than the chest cavity. Technology disclosed in this patent document allows predicting the location of the heart relative to the patient's posterior midline based the patient's demographics. This allows for heart-centric patient placement which enables imaging with a smaller diameter. This is beneficial in CT as a smaller diameter leads to reduced imaging dose.

Once a region of interest (e.g., heart) is identified and delineated within a larger object (e.g., chest), filtering and/or shaping X-ray beams before they reach the patient as well as modulating the X-ray tube current (and/or voltage) as a function of gantry position are tailored to the region of interest according to the disclosed technology. Given the heterogeneity of attenuation, tailoring the acquisition for the region of interest allows for either a dose reduction for the same image quality or an improvement in image quality for the same level of dose.

While current CT imaging systems are capable of imaging a large field-of-view (FOV) on the order of 50 cm in diameter, many clinical tasks interrogate and analyze a smaller region of interest (ROI). For example, single organ studies such as coronary artery calcium (CAC) and coronary angiography (CCTA) are focused on the heart, which only takes up approximately ⅓ of the chest cross-section. Despite this focus, conventional cardiac imaging irradiates the entire patient cross-section to avoid limited field-of-view artifacts. Additionally, techniques to improve dose efficiency such as automated exposure control (AEC) optimize image quality throughout the FOV. Thus, despite clinical interest being limited to the ROI, conventional imaging fails to realize potential dose efficiencies from task-specific tailoring. Therefore, the need still exists to develop CT imaging technologies and systems that target specific region of interest and reduce overall radiation.

X-ray Computed Tomography (CT) is a powerful medical imaging modality with many clinical applications including screening for disease, diagnosis, and preprocedural planning. The ability to rapidly (≤250 ms) acquire a volumetric image at submillimeter resolution has led to its widespread use. Despite the benefits of CT imaging, the use of ionizing radiation and increase in the number of CT scans per capita has raised concern about accumulation of radiation dose in the population. To allay this concern, acquisition protocols specify a variety of parameters including beam-shaping filtration, tube current and voltage, and reconstruction methods which are tuned to reduce dose while providing sufficient task-specific image quality.

The drive to reduce radiation dose and interest in ROI-focused applications of CT have spurred the development of technologies to optimize dose delivery. Fluence field modulation was proposed as a framework for optimization of X-ray fluence to achieve dose and image quality objectives. Various dynamic filtration schemas have been proposed including wedge-systems, piecewise-linear attenuators, variable attenuation fluid-based filters, and multiple aperture devices (MADs). Although dynamic filtration allows for high degrees of fluence field customization, the proposed implementations require substantial modification of current scanner designs. Conversely, static beam-shaping filtration is a standard component of clinical scanners. Static filtration represents a promising technique for ROI imaging that is compatible with current scanner design.

Certain implementations of the technology disclosed in this patent document tailor static beam-shaping filtration to the task of imaging the heart within the larger chest cavity. Furthermore, the disclosed technology includes techniques to tailor tube current modulation to improve image quality in ROI imaging. The technology disclosed herein can enable substantial reductions in delivered dose while preserving task-specific image quality.

We developed a two-dimensional digital imaging phantom to represent an axial slice through the human chest cavity with contrast enhancement in the left and right ventricles. Two variants were designed, one representing a patient with a normal body-mass index (BMI) as well as another representing a patient with increased BMI.

Figure 1B:
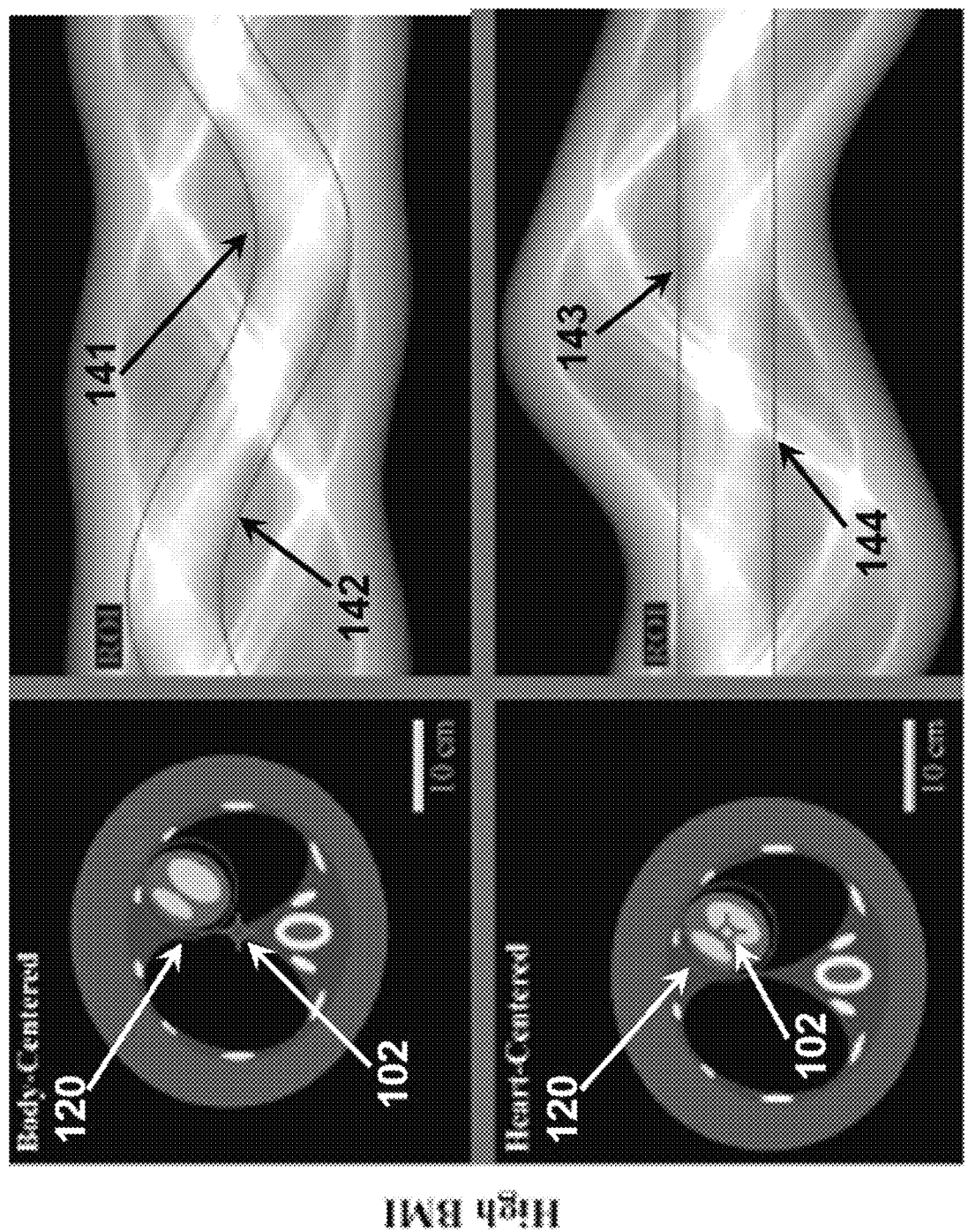
FIG. 1B shows an anthropomorphic digital phantom for a high body mass index (BMI) person representing an axial slice of the person's chest cavity.

FIGS. 1A and 1B show anthropomorphic digital phantoms for a normal person (FIG. 1A) and a high BMI person (FIG. 1B) representing an axial slice of the person's chest cavity. For both phantoms, the same 10.4 cm diameter ROI encapsulated the heart (circles 110 and 120 in FIGS. 1A and 1B, respectively). Two positioning protocols were used: "Body-Centered" such that the isocenter (101 in FIG. 1A; 102 in FIG. 1B) is co-located with the geometrical center of the body and "Heart-Centered" such that the ROI is located at the isocenter. An isocenter is typically the point in space through which the central rays of the radiation beams pass. Phantoms were analytically forward projected to their respective sinograms. With "Body-Centered" positioning, the ROI (curves 131 and 132 in FIG. 1A; curves 141 and 142 in FIG. 1B) oscillates in the sinogram. However, with "Heart-Centered" positioning, the ROI is fixed (curves 133 and 134 in FIG. 1A; curves 143 and 144 in FIG. 1B).

The phantoms were constructed from elliptical regions of various linear attenuation coefficients $\mu(x,y)$ typical of tissues within the human body such as bone, muscle, adipose, blood, and blood mixed with iodinated X-ray contrast agent. Linear attenuation values were established using the NIST table of X-ray attenuation coefficients at 100 keV effective beam energy, as tabulated in Table A1.

We developed a CT scanner simulation using a fan-beam geometry based on a single-source clinical scanner with $N_d$=896 detectors per row, FA=49.2° fan angle, SAD=600 mm source-axis distance, SDD=1072 mm source-detector distance, and no flying focal spot using MATLAB (MathWorks, Natick MA, USA). The phantom was positioned either "body-centered" such that isocenter was colocated with the geometrical center of the body, or "heart-centered" such that the heart ROI was located at the isocenter.

The phantom linear attenuation field $\mu(x,y)$ was forward projected to the sinogram $g(\gamma,\beta)$ via the fan-beam transform $$g(\gamma,\beta)=\int_{x_S(\beta)}^{x_D(\gamma,\beta)}\mu(x,y)ds. \tag{1}$$

where $\gamma \in [-FA/2, FA/2]$ is the detector angle, $\beta \in [0, 2\pi]$ is the view angle, $x_S$ is the source position, and $x_D$ is the detector position. The construction of the phantom from elliptical regions enabled analytical evaluation of (1). Scatter and a finite focal spot size were not incorporated in the forward projection model and a monoenergetic (E=100 keV) beam approximation was used.

The simulation was developed using the following mathematical model of X-ray photon transport. The discrete detectors and view angles were indexed by $\gamma_i$ and $\beta_j$, respectively, where $i \in \{1, \ldots, N_d\}$ and $j \in \{1, \ldots, N_p\}$, with $N_p$ denoting the number of projections acquired per gantry rotation. To simulate the stochastic effects of photon counting and generate realistic noise, the number of photons detected at $\gamma_i$ and $\beta_j$ was computed as a realization of the random variable $\hat{n}_{ij} \sim \text{Poisson}(n_{ij})$ where $$n_{ij}=C\int_{\gamma_i-\frac{\Delta\gamma}{2}}^{\gamma_i+\frac{\Delta\gamma}{2}}\int_{\beta_j-\frac{\Delta\beta}{2}}^{\beta_j+\frac{\Delta\beta}{2}}\psi(\gamma)m(\beta)\exp(-g(\gamma,\beta))d\beta d\gamma, \tag{2}$$

is the expected photon count, $\Delta\gamma=FA/N_d$ is the detector extent, $\Delta\beta=2\pi/N_p$ is the gantry rotation increment, $\psi(\gamma)$ is the beam-shaping filter modulation, and $m(\beta)$ is the tube current modulation. We evaluate (2) via numerical integration. The constant of proportionality is defined by $C=I_o w \eta_s \eta_d / q_e \Omega \text{SDD}$, where $I_o$ is the average tube current, w is the axial detector width, $\eta_s$ is the source efficiency, $\eta_d$ is the detector efficiency, $q_e$ is the electron charge, $\Omega$ is the gantry rotation speed, and SDD is the source-detector distance. C is a dimensionless measure of X-ray beam intensity.

In the absence of the phantom, the scanner would detect in expectation a calibrated photon count $c_{ij}$ given by (2) when $g(\gamma,\beta)=0$. The imaged sinogram is defined by $\hat{g}_{ij}=-\log(\hat{n}_{ij}/c_{ij})$. The sinogram error $\epsilon_{ij}$ is defined as the difference between the imaged and true sinogram and is computed by $\epsilon_{ij}/\hat{g}_{ij}-g_{ij}$, where $g_{ij}=g(\gamma_i,\beta_j)$. We define noise index as $NI_{ij}=n_{ij}^{-1/2}$. We define sinogram noise as $\sigma_{ij}=\sqrt{\text{Var}[\epsilon_{ij}]}$. It can be shown that $$\sigma_{ij} \approx NI_{ij} \propto \frac{1}{\sqrt{C}}. \tag{3}$$

Accordingly, we varied beam intensity C to produce images over a range of clinically-relevant noise levels.

The Nyquist criterion for fan-beam sampling was satisfied. Depending on the acquisition, a sufficient number of projections was acquired to fully reconstruct either the full field-of-view (FOV) or the heart region-of-interest (ROI). $N_p$=4679 and $N_p$=974 projections were acquired per gantry rotation, corresponding to FOV diameter D=50 cm and ROI diameter d=10.4 cm, respectively.

For image reconstruction, rebinning of fan-beam data was performed using bilinear interpolation of the fan-beam sinogram to generate 2× up sampled parallel-beam data. Oversampling was performed to avoid interpolation artifacts. Then, convolution backprojection was performed using a Ram-Lak filter and images were downsampled to final pixel dimension 0.79×0.79 mm, creating the noisy image $\hat{\mu}(x,y)$.

CT systems typically pass the X-ray beam through a beam-shaping filter placed between the source and imaging target. The purpose of shaping the beam is to equalize the photon flux as a function of detector angle which homogenizes the noise in the sinogram and reduces dose delivered to the periphery of the imaging target. Conventionally, the "bowtie" design compensates for attenuation variation due to a circular cylinder of diameter D, concentric with the scanner isocenter, and with a homogeneous linear attenuation coefficient $\mu_p$, mimicking the attenuation characteristics of human tissue. For D=50 cm, $\mu_p$=0.203 cm$^{-1}$, and SAD=60 cm, the bowtie filter modulation $\psi(\gamma)$ is log-plotted as a curve 210 in FIG. 2A. The "bowtie" permits the highest fluence in the center of the fan to compensate for higher attenuation there, and gradually reduces fluence in the periphery as the attenuation decreases accordingly.

Figure 2A:
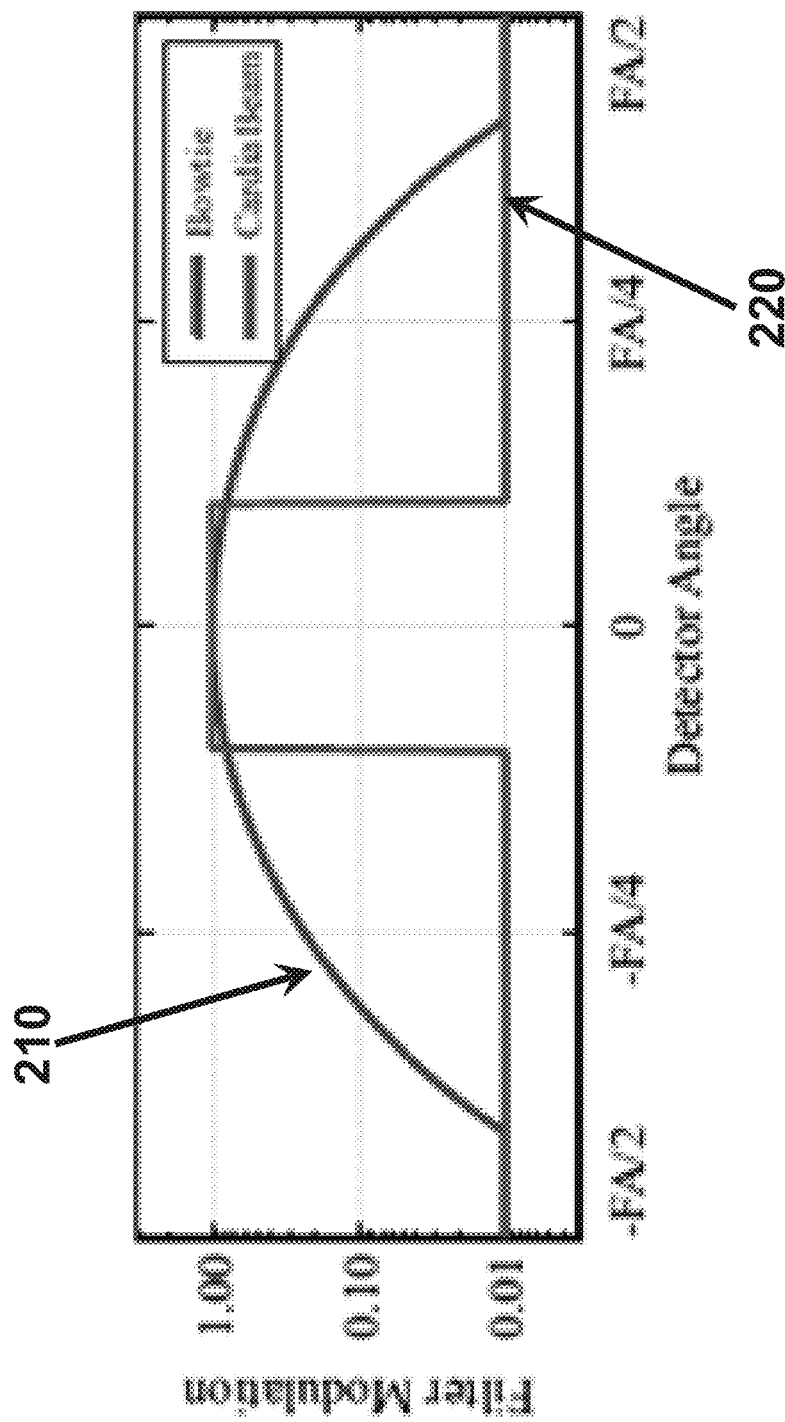
FIG. 2A illustrates modulation of X-ray fluence as a function of detector angle using a beam-shaping filter.

FIG. 2A illustrates how a beam-shaping filter modulates the X-ray fluence as a function of detector angle, characterized by the filter modulation $\psi(\gamma)$. The conventional "bowtie" filter is shown by the curve 210 and CardiaBeam by the curve 220. CardiaBeam dramatically reduces X-ray fluence to peripheral tissues.

Figure 2B:
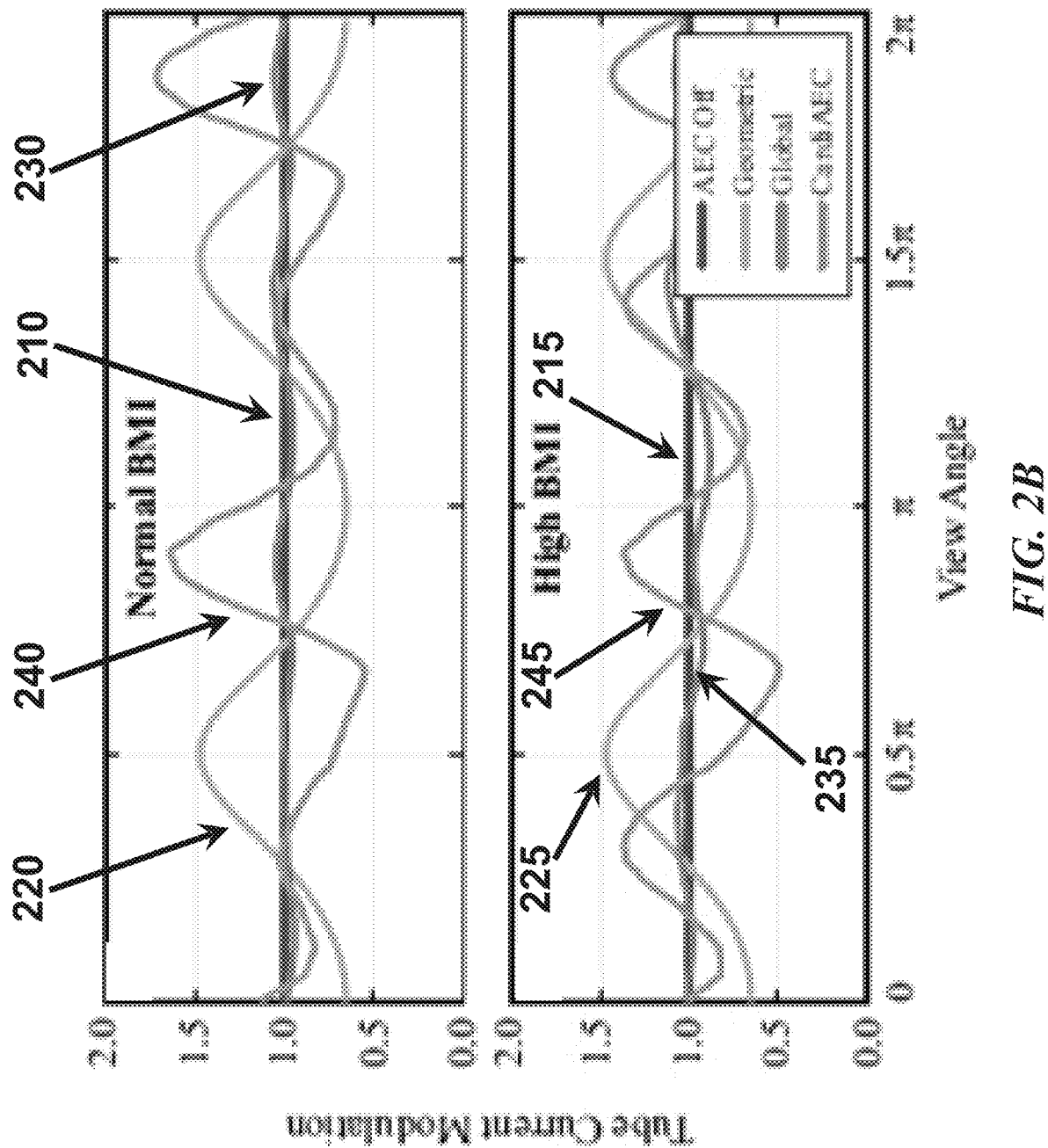
FIG. 2B illustrates various models for view-wise modulation of X-ray tube current.

Tube current modulation accounts for patient-specific view-dependent attenuation variation. Various models for view-wise attenuation produce different modulation functions. FIG. 2B shows Geometric AEC (curves 220 and 225 for normal and high BMI patients, respectively), which is based on an elliptical model of the patient cross-section. FIG. 2B also shows Global AEC (curves 230 and 235 for normal and high BMI patients, respectively) which equalizes, view-wise, patient-averaged noise index. FIG. 2B further shows modulation according to the disclosed technology, termed CardiAEC (curves 240 and 245 for normal and high BMI patients, respectively), which equalizes the view-wise heart-averaged noise index. Note that in anteroposterior (AP) views ($\beta \approx 0.8\pi$), CardiAEC increases tube current to compensate for superposition of the heart and spine, whereas the others fail to account for this high attenuation. Curves 210 and 215 in FIG. 2B correspond to absence of tube current modulation.

In purely local tomography, only those rays which pass from the source through the ROI are collected, resulting in a truncated sinogram. The problem of reconstructing the inside of the ROI from truncated projections is called the interior tomography problem and has been shown to be, in general, unsolvable. Without correction, naive filtered back-projection produces a high intensity, low frequency "cupping" artifact in the reconstructed images. Certain extrapolation heuristics can be applied to the sinogram to reduce the qualitative impact of these artifacts, but they do not guarantee bias-free reconstruction.

CardiaBeam X-ray fluence modulation (also referred to as X-ray fluence attenuation) according to the disclosed technology reduces X-ray fluence to a small, albeit nonzero, value for rays outside the ROI. This reduced value is given by $\psi_{min}=1-1/f_o$, where $f_o$ is the filter modulation factor. By modulating the beam, measurements outside of the ROI will be a noisy estimate of the attenuation along those rays. The ROI is repositioned to the isocenter; due to "heart-centered" positioning, forward projection of the ROI corresponds to a central strip in the sinogram (between lines 133 and 134 in FIG. 1A and between lines 143 and 144 in FIG. 1B). Thus, modulation of the fluence field is accomplished with a static filter. For a ROI of diameter d=10.4 cm and $f_o$=100, the CardiaBeam modulation is log-plotted as the curve 220 in FIG. 2A. Note that the fluence is reduced to a small, albeit nonzero, value outside the ROI, in this case $\psi_{min}$=0.01.

Fluence is reduced in the periphery of the imaging target outside of the ROI, which has the effect of dramatically reducing dose delivered to those tissues. However, nonzero fluence effectively prevents local tomography artifacts by obtaining noisy projection information about the entire imaging target, thus permitting conventional reconstruction.

Automated exposure control (AEC) is a general term for algorithms that select and modulate the X-ray tube current to achieve image quality and dose goals. The goal of tube current modulation (TCM) is to equalize the photon flux on the detectors as a function of view angle to reduce photon starvation. Reduction in photon starvation produces reconstructed images with less spatially structured noise: streak artifacts are diminished. There are several conventional approaches which use different models for view-wise attenuation variation. In practice, information about the patient-specific geometry and attenuation characteristics is prospectively acquired from low-dose CT projection radiographs (scouts).

Geometrically, the human chest cavity is dominated by asymmetry between the anteroposterior and lateral dimensions. Using an elliptical phantom of homogeneous, tissue-equivalent attenuation $\mu_p$ and semimajor and semiminor axes $d_{lt}$ and $d_{ap}$, respectively, we derive the "Geometric" TCM curves 220 and 225 shown in FIG. 2B. We call this the "Geometric" TCM as its model of attenuation variation is a function of imaging target geometry which is, in practice, estimated from apparent patient dimensions in anteroposterior and lateral scouts.

It can be shown that noise index obeys $$NI \propto (m(\beta)\psi(\gamma)\exp(-g(\gamma,\beta)))^{-1/2}. \quad (4)$$

To equalize the average noise index in a region over all view angles, the resulting modulation function is $$m_{NI}(\beta) = c_{NI} \left( \int_{\mathcal{G}(\beta)} (\psi(\gamma)\exp(-g(\gamma,\beta)))^{-\frac{1}{2}} d\gamma \right)^2, \quad (5)$$

where $\mathcal{G}(\beta)$ is the set of detector angles that contains the region at view angle $\beta$ and $c_{NI}$ is a normalization constant to ensure $$\frac{1}{2\pi} \int_0^{2\pi} m(\beta) d\beta = 1.$$

In the absence of a task-specific region choice, the calculation can be based on the average attenuation of the entire imaging target. This "Global" TCM is shown by the curves 230 and 235 in FIG. 2B. For a task-specific acquisition, the disclosed technology uses CardiAEC, a TCM scheme which is tailored to imaging of a region of interest (e.g., heart). This new CardiAEC modulation function accounts for attenuation variations specifically within the ROI and is shown by curves 240 and 245 in FIG. 2B. Of note is the observation that CardiAEC increases the tube current in AP-PA views. This effect is due to the spine and contrast-enhanced ventricular blood pool superposing in this orientation, and CardiAEC compensating for the increased attenuation. Since the other approaches are not tailored to the ROI, they fail to account for this local attenuation variation.

Image quality for each acquisition scheme was quantified using the contrast-to-noise ratio (CNR) between the contrast-enhanced left ventricular blood pool and myocardium $$CNR = \frac{|\mu_{lv} - \mu_{myo}|}{\sqrt{\sigma_{lv}^2 + \sigma_{myo}^2}}, \quad (6)$$

where $\mu_{(\cdot)}$ and $\sigma_{(\cdot)}$ denote mean and standard deviation of CT number in each region, respectively. For each protocol, we fit the model $CNR = \mathcal{A} u_{pat}^{1/2}$, where $u_{pat}$ is patient dose and $\mathcal{A}$ is the constant of proportionality. Values of $\mathcal{A}$ are used for dose reduction quantification between protocols.

Image quality was also quantified with RMS image error in the ROI:

$$e_{ROI} = \sqrt{\frac{1}{|ROI|} \iint_{ROI} (\hat{\mu}(x,y) - \mu(x,y))^2 dx dy}. \quad (7)$$

Statistics of CNR and $e_{ROI}$ are reported as sample mean and standard deviation from 21 realizations per scanning condition. We fit the power law $e_{ROI} = \mathcal{B} u_{pat}^{-p_e} + e_o$ to account for image noise as well as bias due to the nonlinearity of the log transform of attenuation data.

To further understand the improvements provided by the technology disclosed herein, particularly in the case of TCM, we developed two methods of analyzing structured CT noise. When noise index is equalized as a function of view angle, the backprojected image noise is less textured. One mechanism of streak artifact generation is an outlier in the sinogram error $\epsilon$, via backprojection, producing structured noise in the image.

We assessed the prevalence of sinogram error outliers using quantile-quantile (q-q) plots. The normal q-q plot is constructed by plotting the empirical quantiles of the sinogram error $\epsilon$ (within the ROI) against theoretical quantiles of a normal distribution with the same mean and variance as the data. In our q-q plots, the data is normalized by the intraquartile range (IQR) to give a scale-invariant visualization. The closer the data lies to the line of unity, the more the distribution exhibits normality. When the data deviates away from the line of unity (upward to the right and downward to the left), then the distribution has a higher prevalence of outliers (a heavy-tailed distribution). We used these q-q plots to semi-quantitatively assess prevalence of sinogram outliers generated by different tube current modulation schema.

To further quantify outlier prevalence, we used a parametric approach based on statistics of extremes. We fit a scaled Student's t distribution using maximum likelihood estimation to the sinogram error $\epsilon$ within the ROI. Fitting yielded two parameters: s which quantifies sinogram noise and $\chi$ which quantifies the prevalence of outliers. Statistics of s and $\chi$ are reported as sample mean and standard deviation from 21 realizations at each scanning condition.

For noise, we fit the model $s = \mathcal{C} u_{pat}^{-1/2}$. The constants of proportionality C are used to quantify noise reductions. For outlier prevalence, we fit the power law $\chi = \mathcal{D} u_{pat}^{-p_\chi} + \chi_o$. The parameter $\chi_o$ is the asymptotic outlier prevalence. Values of $\chi_o$ are used to compare outlier reduction between schema.

To quantify radiation dose, we used an anatomically-specific model. We chose to measure patient dose as opposed to dose index because of its more direct connection to patient risk. The photon flux field $\phi(x,y,\beta)$ (photon arrival rate per unit area) is given by $$\phi(x,y,\beta) = \frac{C\Omega SDD}{\eta_d w} m(\beta) \psi(\gamma) \exp\left(-\int_{x_S(\beta)}^{x(x,y)} \mu(x,y) ds\right), \quad (8)$$

where $x(x,y)$ is a position at which the photon flux is to be evaluated. Our model does not incorporate scatter or finite focal spot size and uses a monoenergetic beam. We aim to quantify the relative patient dose between scanning protocols. We expect the physical phenomena leading to differences in dose between protocols to be primarily captured by this simpler model.

Computation of the photon flux field was performed by numerical integration of (8). The dose rate is given by $$\dot{u}(x,y,\beta) = \frac{\phi(x,y,\beta)\mu_{en}(x,y)E}{\rho(x,y)}, \quad (9)$$

where E is the effective photon energy, $\mu_{en}(x,y)$ is the linear absorption, and $\rho(x,y)$ is the target density. Linear absorption coefficients were derived from the NIST table of X-ray attenuation coefficients at 100 keV effective beam energy and densities were prescribed using commonly accepted values. The dose accumulated during a scan is $$u(x,y) = \frac{1}{\Omega} \int_0^{2\pi} \dot{u}(x,y,\beta) d\beta, \quad (10)$$

where $\Omega$ is the gantry rotation speed. Dose maps were computed by numerical integration of (10).

Regional dose is a density-weighted average of u(x,y). Let $\mathcal{R}$ be the region containing the patient's body. Then, $$u_{pat} = \frac{\int_{\mathcal{R}} u(x,y) \rho(x,y) dx}{\int_{\mathcal{R}} \rho(x,y) dx} \quad (11)$$

is the patient dose, evaluated via numerical integration.

Using both the normal and high BMI phantoms, we simulated the acquisition protocols in Table I with varying beam intensity $\mathcal{C}$. Note that CardiaBeam acquisitions used "heart-centered" positioning, while all others were "body-centered."

TABLE I

| Acquisition Protocols | | | | |
|---|---|---|---|---|
| Name | Filter | AEC | Sampling | Position |
| Baseline | Bowtie | None | FOV | Body |
| Filter | CardiaBeam | None | ROI | Heart |
| AEC1 | Bowtie | Geometric | FOV | Body |
| AEC2 | Bowtie | Global | FOV | Body |
| AEC3 | Bowtie | CardiAEC | FOV | Body |
| Combined | CardiaBeam | CardiAEC | ROI | Heart |

Figure 3:
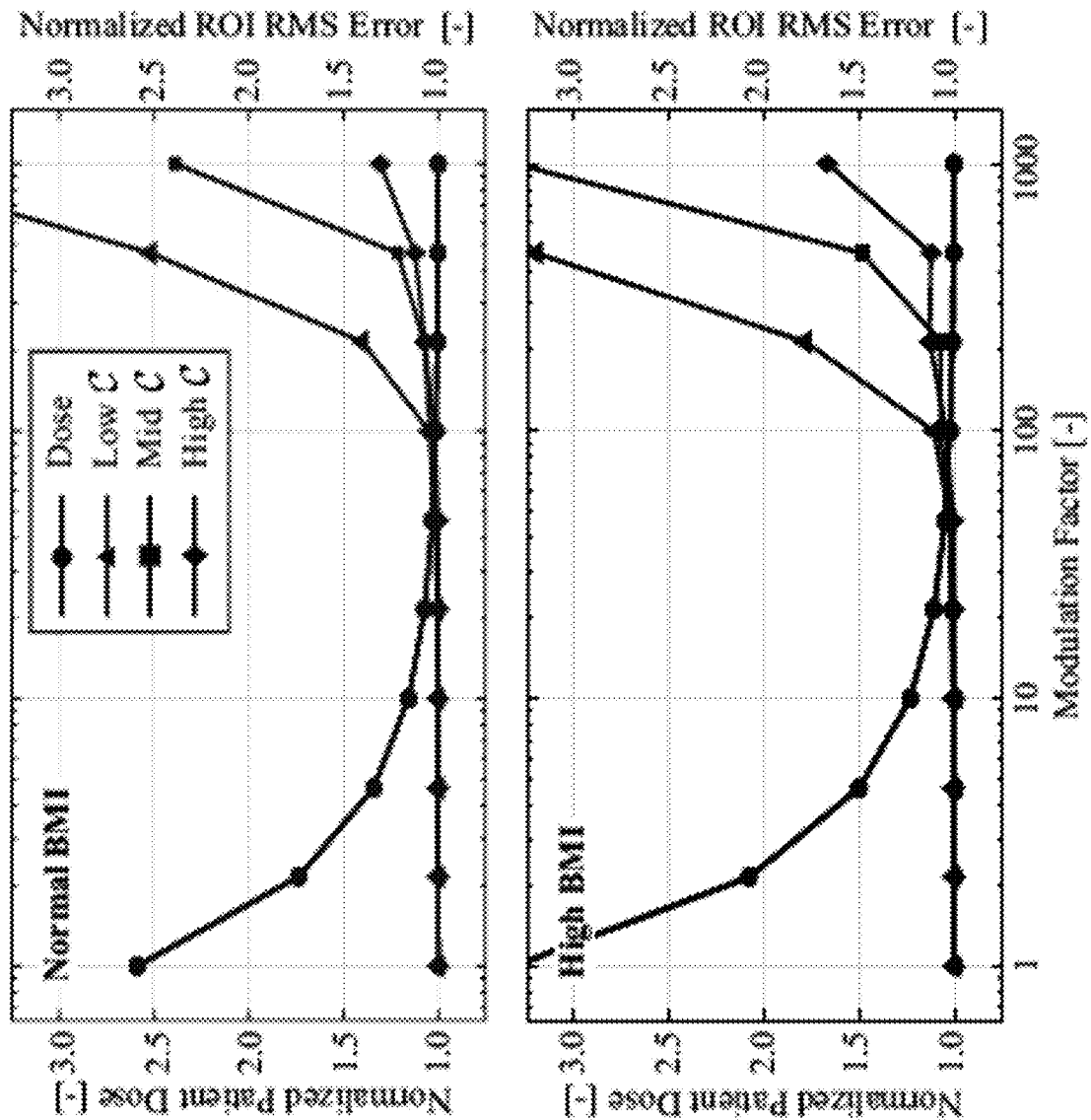
FIG. 3 shows the patient dose and root mean square region of interest image error as a function of the modulation factor for an example implementation of the disclosed technology.

Optimization of the modulation factor $f_o$ was performed by measuring the patient dose $u_{pat}$ and root mean square (RMS) ROI image error $e_{ROI}$ as a function of $f_o$, see FIG. 3. As $f_o$ increases, $u_{pat}$ (gray line) approaches its theoretical minimum at the truncation dose ($f_o \to \infty$). Then, we plot $e_{ROI}$ for three different scanning conditions: beam intensity C was varied such that CNR=2, 4, and 6 when $f_o$=100, respectively. The image error is normalized by its theoretical minimum, the full fluence value ($f_o$=1). Across scanning conditions, we observe that at $f_o \approx 100$, there is a nearly optimal tradeoff between patient dose and image quality: nearly all the dose savings of local tomography ($u_{pat}$ is ≤2.3% above minimum) are achieved with nearly none of the image quality degradation ($e_{ROI}$ is ≤10% above minimum). Thus, $f_o$=100 was selected for further analysis of CardiaBeam.

FIG. 3 illustrates trade-off between patient dose $u_{pat}$ and ROI RMS image error $e_{ROI}$ as a function of CardiaBeam modulation factor $f_o$, each normalized by their theoretical minima. As $f_o$ increases, patient dose (gray line) approaches theoretical minimum (full truncation when $f_o \to \infty$). For three different scanning conditions (beam intensity C chosen such that CNR=2, 4, and 6 when $f_o$=100), we plot $e_{ROI}$. As $f_o$ increases, $e_{ROI}$ diverges from its theoretical minimum (full fluence when $F_o$=1). We observe a nearly optimal tradeoff at $f_o \approx 100$: nearly all the dose savings of local tomography are achieved with nearly none of the image quality degradation. This observation holds across scanning conditions.

Figure 4:
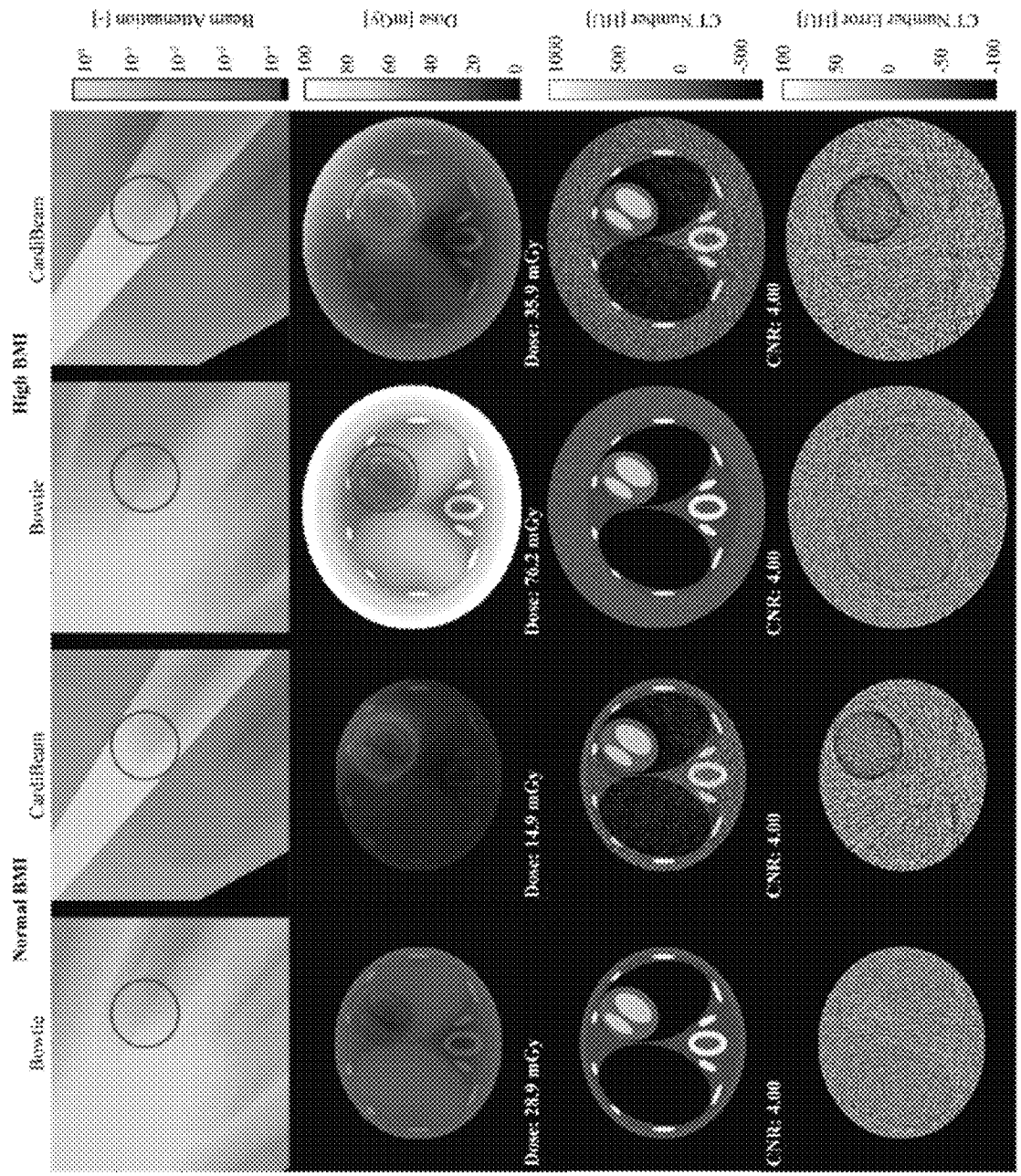
FIG. 4 illustrates beam-shaping, delivery of dose, image quality, and image error for a conventional beam-shaping filter and a beam-shaping filter according to an example embodiment of the disclosed technology.

We compared the performance of CardiaBeam beam-shaping filter according to the disclosed technology to that of the conventional bowtie filter. FIG. 4 illustrates the beam-shaping delivery of dose, image quality, and image error at CNR=4.00. In both the normal and high BMI phantoms, CardiaBeam enables a reduction in patient dose: 28.9 mGy to 14.9 mGy and 76.2 mGy to 35.9 mGy, respectively. The patient dose reduction is achieved by restricting the width of the high fluence beam to the ROI. The reconstructed images and error maps illustrate the preservation of image quality within the ROI. The reduced fluence produces increased noise and streaking in the surrounding tissue.

FIG. 4 illustrates dose reductions achieved using CardiaBeam in normal and high BMI phantoms. First and third column depict result with bowtie filter whereas second and fourth column depict result with CardiaBeam. First row in FIG. 4 shows beam attenuation at a representative gantry angle. For CardiaBeam, beam is highly attenuated outside of the ROI. Second row in FIG. 4 shows dose distribution with CNR=4.0. For CardiaBeam, the dose is concentrated in the ROI and average patient dose is reduced. Reconstructed maps of CT Number (third row in FIG. 4, win/lvl=1700/200) and corresponding error map (fourth row in FIG. 4, win/lvl=1600/0). We observe similar noise texture and error inside the ROI between the bowtie and CardiaBeam. Note that despite reductions in patient dose with CardiaBeam, CNR is preserved.

Figure 5:
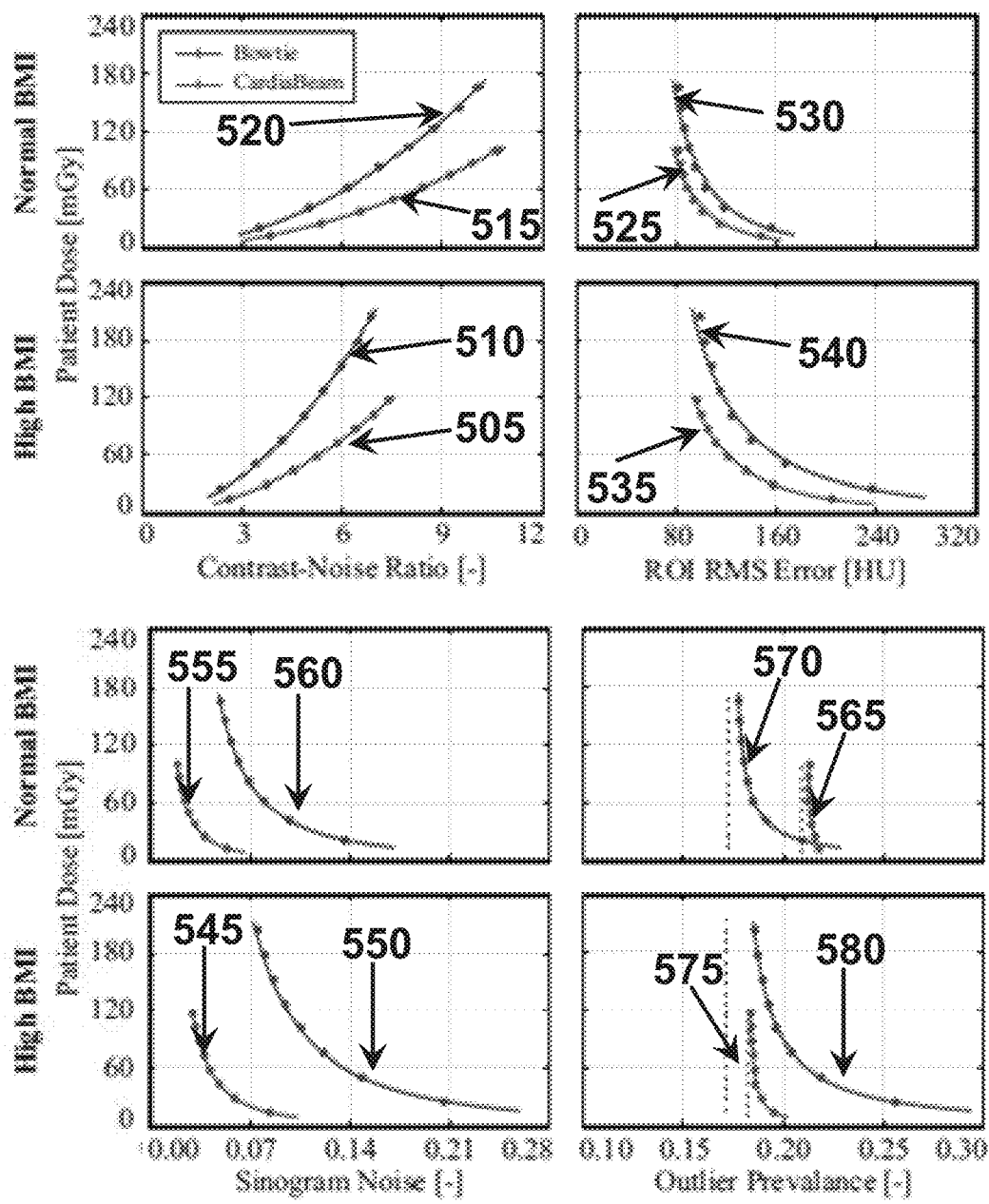
FIG. 5 illustrates relationships between image quality and dose in normal and high BMI phantoms for a conventional beam-shaping filter and a beam-shaping filter according to an example embodiment of the disclosed technology.

FIG. 5 compares the CNR, ROI RMS error, sinogram noise, and outlier prevalence for the filters as a function of dose. Model parameters can be found in Table B 1. We find that for fixed CNR, CardiaBeam decreases dose by 46.0±0.4% and 50.3±0.3% in the normal and high BMI phantoms, respectively. Similarly, for fixed sinogram noise, dose is decreased by 90.81%±0.02% and 90.75%±0.04%, respectively.

Figure 6:
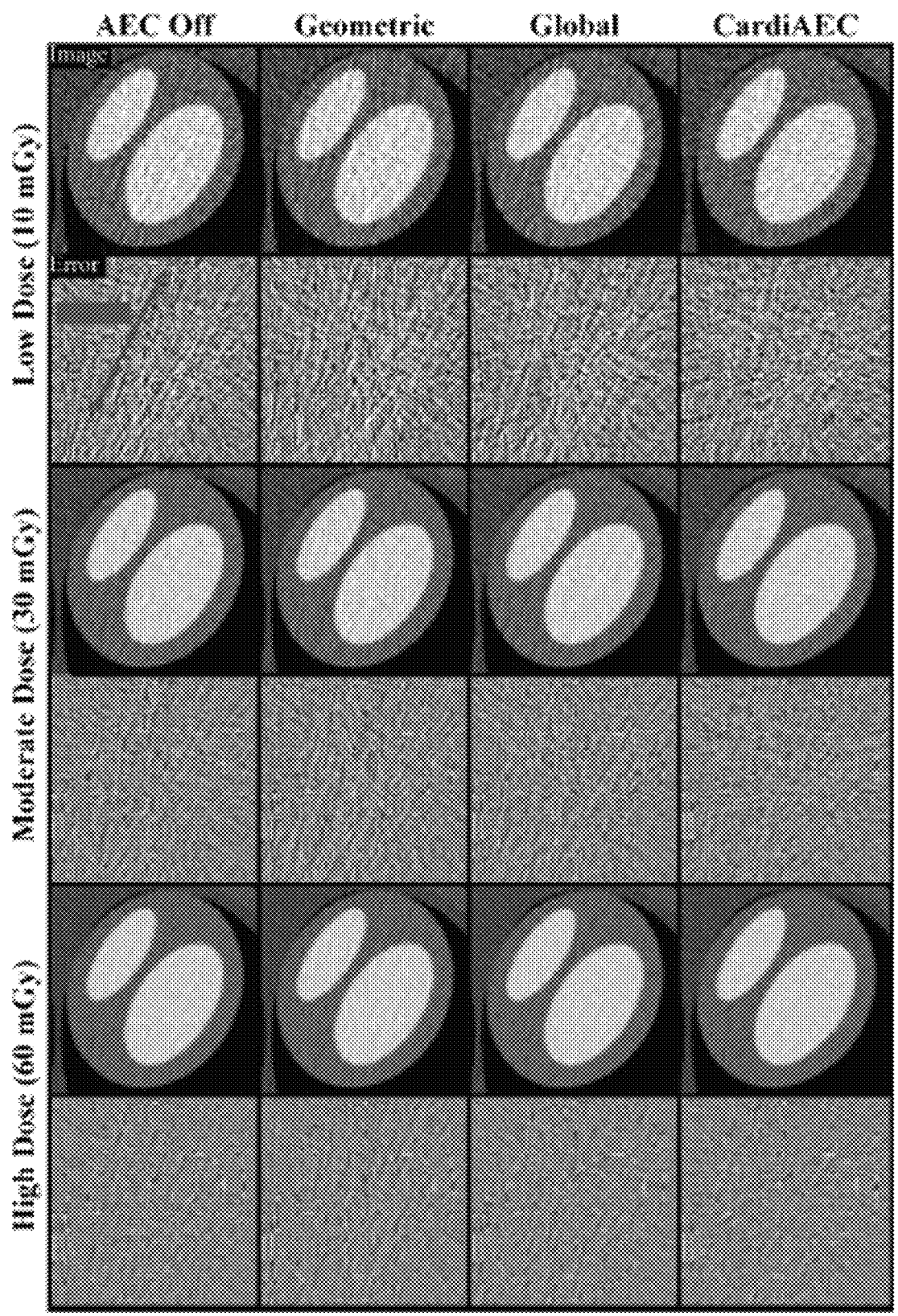
FIG. 6 shows reconstructed images and errors at low, moderate, and high dose levels for different tube current modulation (TCM) schemas.

FIG. 5 illustrates relationships between image quality (CNR, ROIRMS error, sinogram noise, and outlier prevalence) and dose in normal and high BMI phantoms with bowtie and CardiaBeam. Trends across scanning conditions show that in both normal and high BMI phantoms, dose is reduced when using CardiaBeam. Curves 505, 515, 525, 535, 545, 555, 565, and 575 in FIG. 5 correspond to a CardiaBeam filter according to the disclosed technology. Curves 510, 520, 530, 540, 550, 560, 570, and 580 in FIG. 5 correspond to a conventional bowtie filter A visual assessment of the TCM schema is shown in FIG. 6. We observe streaks from lower left to upper right in the first three columns, due to high attenuation in the AP-PA views. We observe that CardiAEC reduces streak artifacts.

FIG. 6 shows reconstructed images and errors at low, moderate, and high dose levels for different tube current modulation schemas. First column in FIG. 6 corresponds to AEC Off. Across dose levels, the images contain streaks which decrease in strength as dose increases. Second column in FIG. 6 corresponds to Geometric AEC. Third column in FIG. 6 corresponds to Global AEC. Results are similar, streaks persist. Fourth column in FIG. 6 corresponds to CardiAEC according to the disclosed technology. Noise is less structured and streaks are reduced.

Figure 7:
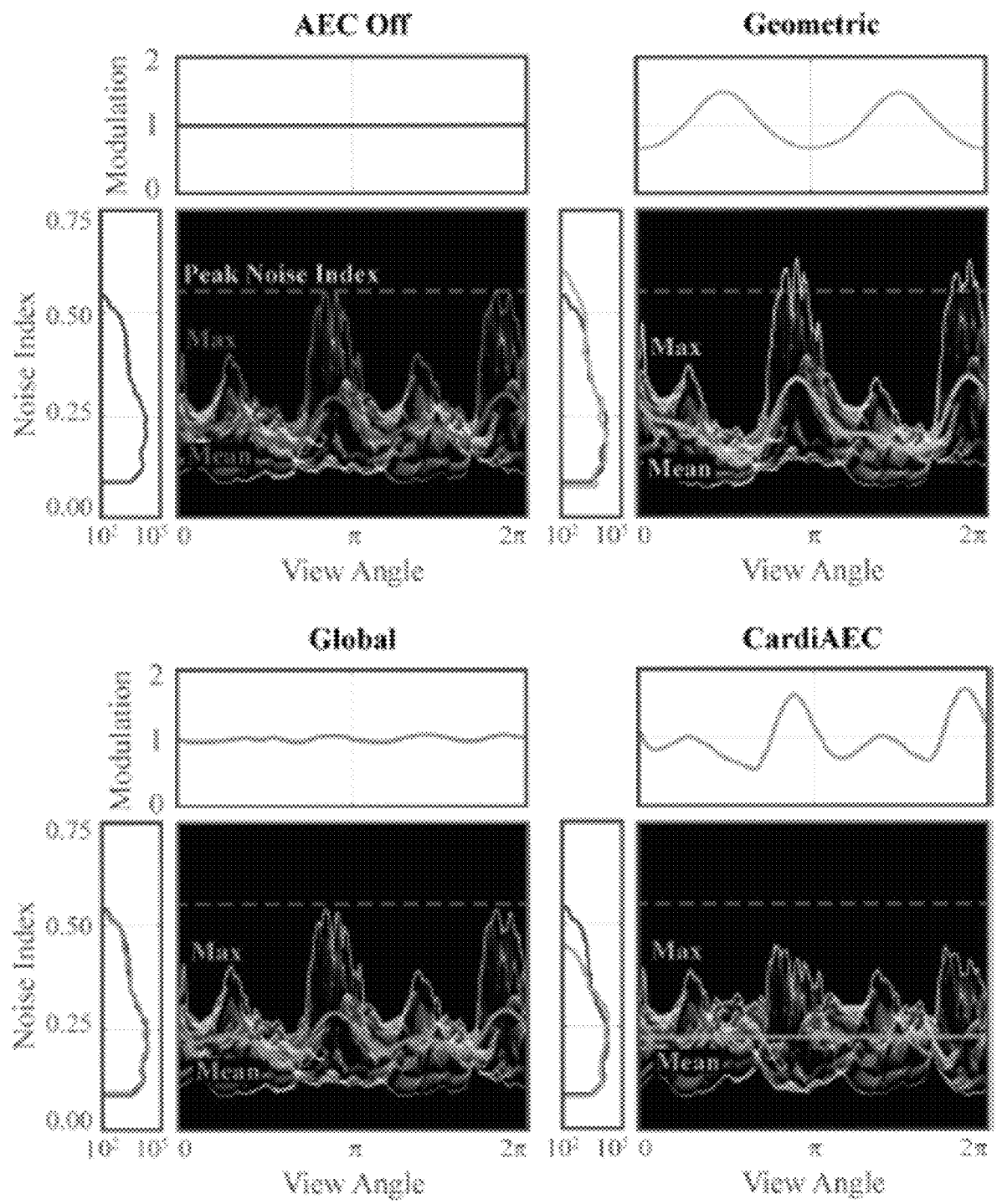
FIG. 7 shows a comparison of noise index distribution for different TCM schemas.

FIG. 7 illustrates the impact of TCM scheme on noise index. For each scheme, we plot a histogram of noise index in the ROI over the entire acquisition (left curves). Here, we see that the variance of noise index is narrowed by CardiAEC compared to the other schemas. The histogram plot of noise index as a function of view angle illustrates that average noise index is successfully equalized by CardiAEC, whereas it oscillates with the other schemas. Additionally, the maximum noise index in the AP-PA views (causing photon starvation streak artifacts) is decreased by CardiAEC.

FIG. 7 shows a comparison of noise index distribution for different TCM schemas. Average noise index is the same for all acquisitions. Upper rows of panels for different TCM schemas in FIG. 7 show modulation functions. Line plots in FIG. 7 show histogram of noise index across all view angles. 'AEC Off' histogram is replicated for comparison across schemas. Colormaps in FIG. 7 show histogram of noise index as a function of view angle. Mean and maximum noise index are plotted as thick and thin lines, respectively. Peak noise index for 'AEC Off' is shown as dashed line. CardiAEC equalizes mean noise index whereas other approaches do not. Additionally, peak noise index in the AP-PA views is decreased in CardiAEC.

Figure 8:
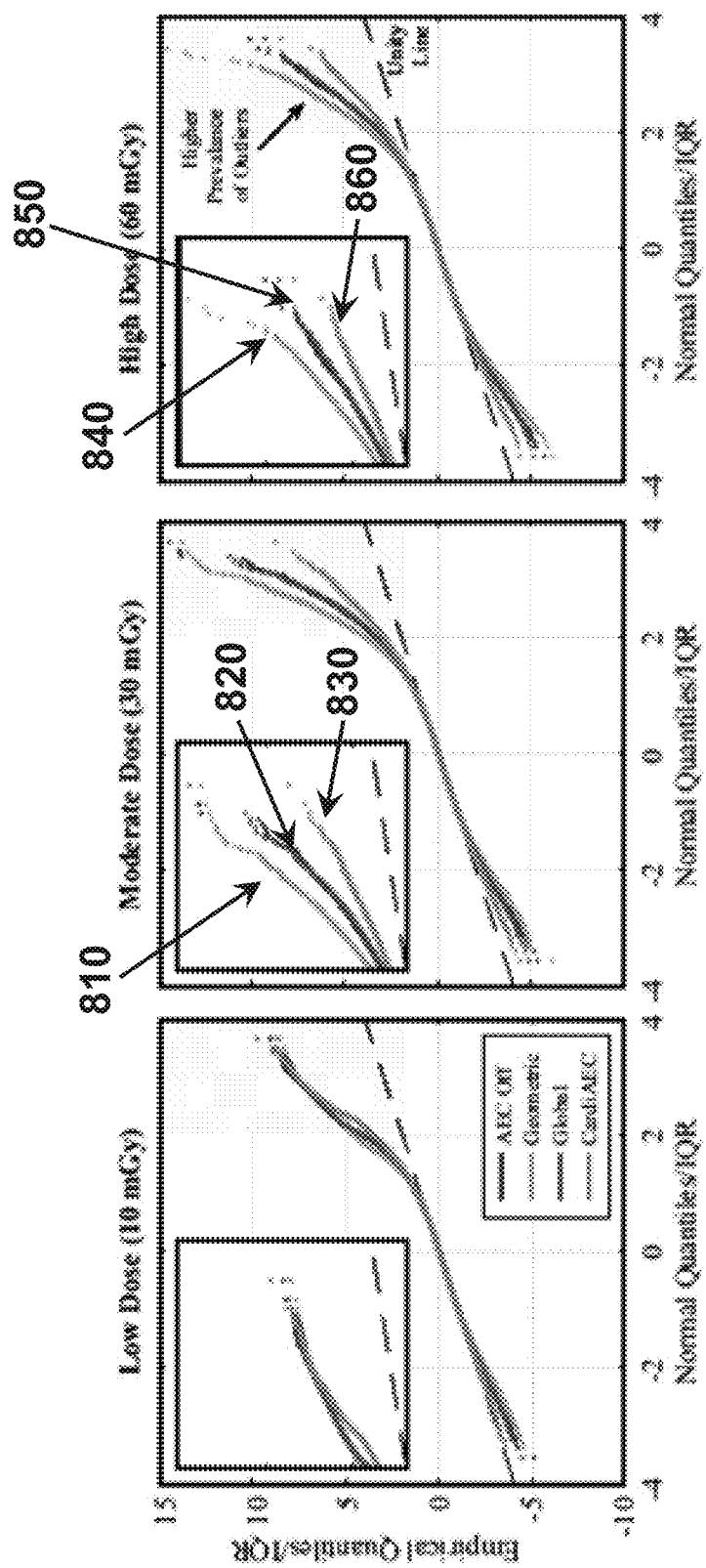
FIG. 8 illustrates semi-quantitative reduction in prevalence of sinogram error outliers for different TCM schemas.

The semi-quantitative reduction in prevalence of sinogram error outliers is depicted in FIG. 8. For low, moderate, and high dose scans, CardiAEC q-q data remain closer to the line of unity, indicating a reduction in the prevalence of outliers. The other schemas depart more from the line of unity, indicating higher prevalence of sinogram outliers. Presence of outliers in error sinogram is a hallmark of streaks in backprojected image. We visualize the prevalence of outliers from each modulation scheme by quantifying the degree to which the sinogram error is heavy-tailed. Empirical quantiles are compared to those of a normal distribution. Since empirical data appears above the line of unity (dashed black) on the right and below on the left, the distributions are heavy-tailed (higher likelihood of outliers). We observe across dose levels, particular at higher dose, that CardiAEC data remain closer to the line of unity, and outlier prevalence is reduced. Curves 810 and 840 in inserts in FIG. 8 correspond to the Geometric TCM schema. Curves 820 and 850 in inserts in FIG. 8 correspond to the Global TCM schema. Curves 830 and 860 in inserts in FIG. 8 correspond to the CardiAEC TCM schema according to the disclosed technology.

Figure 9:
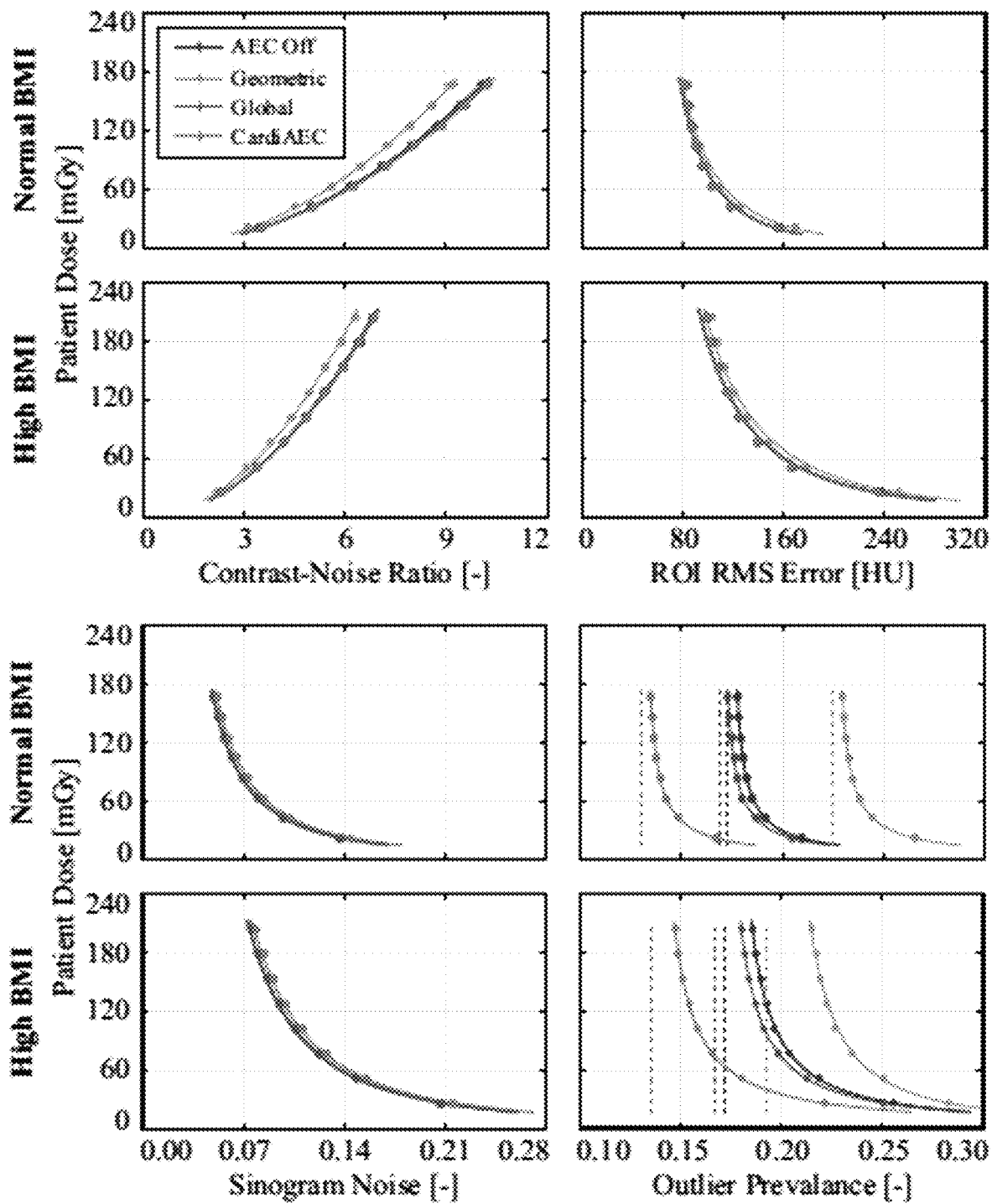
FIG. 9 compares the contrast-to-noise ratio (CNR), sinogram noise, and outlier prevalence for several automatic exposure control (AEC) schemas as a function of dose.

FIG. 9 compares the CNR, sinogram noise, and outlier prevalence amongst the AEC schemas as a function of dose. Model parameters can be found in Table B2. We find that CardiAEC has negligible effect on CNR and sinogram noise. We observe 24.8±0.4% and 21.5±0.4% reductions in outlier prevalence in normal and high BMI phantoms, respectively, providing quantitative explanation for the visual improvement in noise structure provided by CardiAEC.

Figure 10:
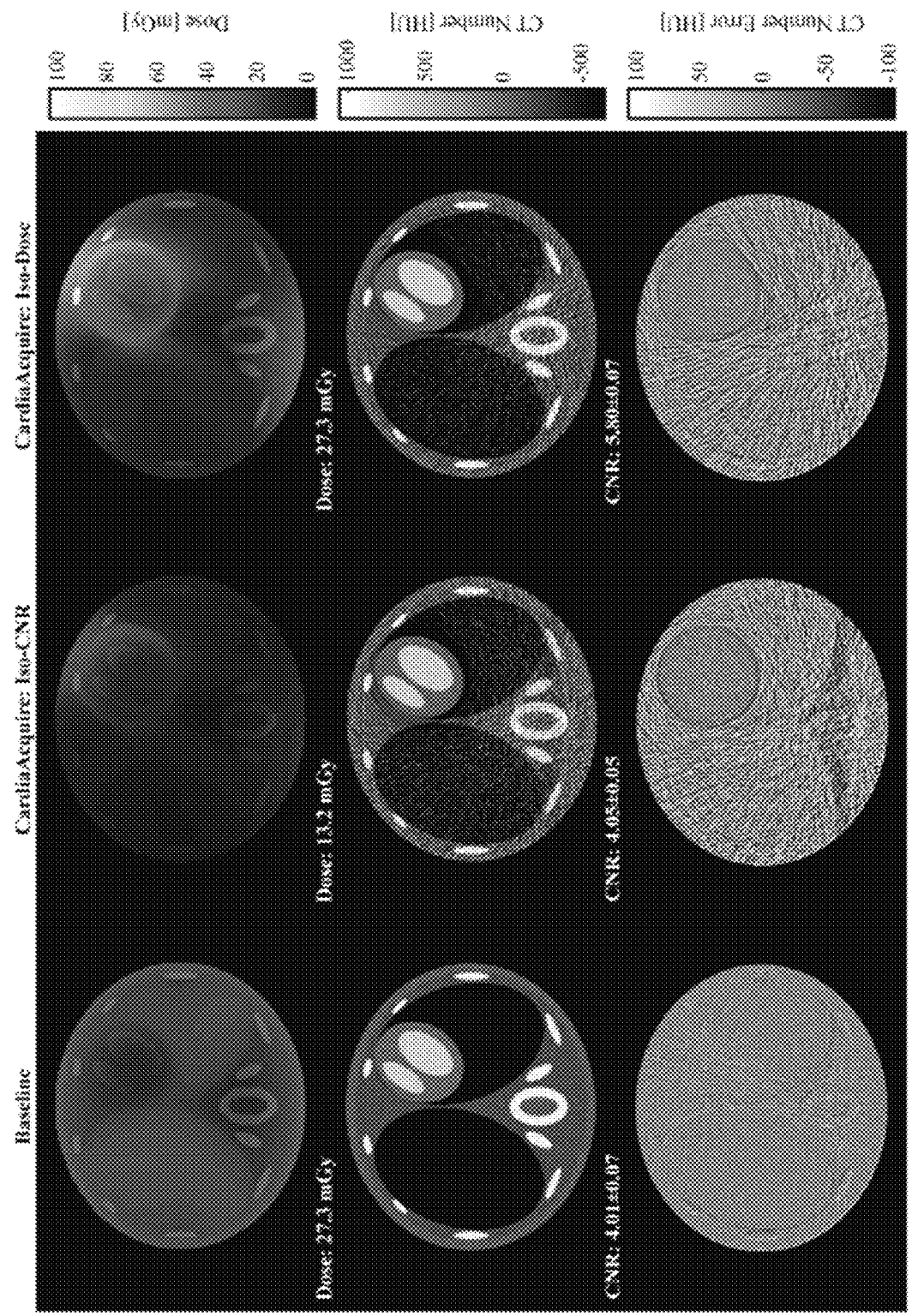
FIG. 10 illustrates a combined effect of a beam-shaping filter and automatic exposure control according to an example implementation of the disclosed technology.

FIG. 10 illustrates the combined effect of both Cardi-Acquire components: CardiaBeam and CardiAEC. For constant CNR, the dose delivered to the patient can be reduced by 51.6%. Reducing the dose to a level similar to that of the conventional approach would lead to a reduction in CNR from 4.00 to 2.73±0.03. On the other hand, for the same dose as in the conventional case, CNR can be increased by 45%. The conventional approach would require an increase in dose from 27.3 mGy to 57.4 mGy to achieve this CNR increase. CardiAcquire improves the dose-image quality trade off for cardiac imaging. In the first column in FIG. 10, we depict the image quality and dose distribution when using the conventional approach—a bowtie filter and the no tube current modulation. Next, in the second column in FIG. 10, we show the results when using CardiAcquire—a combination of the ROI-tailored beam-shaping filter Cardia-Beam and tube current modulation scheme CardiAEC according to the disclosed technology. We can reduce dose by 56% while maintaining the same image quality as the baseline. Third column in FIG. 10 illustrates that we can increase CNR by 45% without requiring more dose than the baseline using the technology disclosed in this patent document.

A tailored acquisition (CardiAcquire) according to the disclosed technology can include the following components: abeam-shaping filter (CardiaBeam) according to the disclosed technology which restricts high-fluence X-rays only to the region of interest, and a tube current modulation scheme (CardiAEC) according to the disclosed technology which equalizes noise index within the ROI. We have demonstrated that CardiAcquire enables significant dose reductions for cardiac CT scanning. The clinical benefits of our approach include the potential to reduce dose to radio-sensitive organs outside of the ROI such as the breasts and lungs. Furthermore, single CT volumes can be acquired for lower dose as compared to the conventional approach, or higher image quality can be achieved at equivalent dose. Also, dynamic scans and/or longitudinal studies can be performed due to the lower dose. We also demonstrated that tailoring of the acquisition to heart imaging according to the disclosed technology improves noise structure within the heart. Such improvements in image quality are clinically relevant because they reduce the potential for diagnosis error due to misidentification of artifacts.

For CardiaBeam, heart-centered patient positioning is possible using scout scans and can be further aided by lateral displacement of the patient table. The ability to install custom beam-shaping filters would be also beneficial. A capability of a scanner to generate a low-dose scout scan over a range of view angles, and embed this information in a new calculation for angular TCM would be beneficial for CardiAEC.

In clinical practice, CardiaBeam will need to be sized to fit actual and typical human heart and chest cavity dimensions and the computation of the CardiAEC curve will depend on patient-specific attenuation characteristics.

TABLE A1

Material Properties of Phantom

| Material | Attenuation [$cm^{-1}$] | Absorption [$cm^{-1}$] | Density [$g \cdot cm^{-3}$] |
| --- | --- | --- | --- |
| Adipose | 0.152 | 0.0219 | 0.90 |
| Bone | 0.343 | 0.0848 | 1.85 |
| Blood w/Contrast | 0.304 | 0.0458 | 1.38 |
| Lung | 0.051 | 0.0077 | 0.30 |
| Muscle | 0.179 | 0.0270 | 1.06 |
| Soft Tissue | 0.169 | 0.0255 | 1.00 |

TABLE B1

Filter Model Parameters

| Phantom | Filter | $\mathcal{A}[mGy^{-1/2}]$ | $R^2$ | $\mathcal{B}[HU \cdot mGy^{Pe}]$ | $P_e$ [-] | $e_o$ [HU] | $R^2$ |
| --- | --- | --- | --- | --- | --- | --- | --- |
| Normal BMI | Bowtie | 0.781 ± 0.002 | 0.997 | 903 ± 38 | 0.7 ± 1.5 | 62.0 ± 1.1 | 0.999 |
|  | CardiaBeam | 1.062 ± 0.003 | 0.997 | 524 ± 22 | 0.7 ± 1.5 | 61.8 ± 1.3 | 0.998 |
| High BMI | Bowtie | 0.779 ± 0.002 | 0.998 | 960 ± 36 | 0.8 ± 1.6 | 63.3 ± 0.9 | 0.999 |
|  | CardiaBeam | 0.792 ± 0.002 | 0.997 | 902 ± 35 | 0.8 ± 1.5 | 62.5 ± 0.9 | 0.999 |

| Phantom | Filter | $\mathcal{C}[mGy^{1/2}]$ | $R^2$ | $\mathcal{D}[mGy^{Px}]$ | $P_x$ [-] | $X_o$ [-] | $R^2$ |
| --- | --- | --- | --- | --- | --- | --- | --- |
| Normal BMI | Bowtie | 0.630 ± 0.001 | 1.000 | 0.74 ± 0.12 | 1.0 ± 2.0 | 0.173 ± 0.001 | 0.990 |
|  | CardiaBeam | 0.191 ± 0.001 | 1.000 | 0.03 ± 0.03 | 0.5 ± 1.7 | 0.209 ± 0.008 | 0.341 |
| High BMI | Bowtie | 0.632 ± 0.001 | 1.000 | 0.79 ± 0.14 | 1.0 ± 2.1 | 0.169 ± 0.001 | 0.989 |
|  | CardiaBeam | 0.664 ± 0.001 | 1.000 | 0.81 ± 0.13 | 1.0 ± 2.1 | 0.130 ± 0.001 | 0.991 |

TABLE B2

Tube Current Modulation Model Parameters

| Phantom | Filter | $\mathcal{A}[mGy^{-1/2}]$ | $R^2$ | $\mathcal{B}[HU \cdot mGy^{Pe}]$ | $P_e$ [-] | $e_o$ [HU] | $R^2$ |
| --- | --- | --- | --- | --- | --- | --- | --- |
| Normal BMI | AEC Off | 0.480 ± 0.001 | 0.997 | 1886 ± 66 | 0.7 ± 1.5 | 60.8 ± 1.6 | 0.999 |
|  | Geometric | 0.681 ± 0.001 | 0.998 | 599 ± 14 | 0.5 ± 0.9 | 26.0 ± 4.4 | 0.999 |
|  | Global | 0.781 ± 0.002 | 0.997 | 903 ± 38 | 0.7 ± 1.5 | 62.0 ± 1.1 | 0.999 |
|  | CardiAEC | 0.708 ± 0.002 | 0.996 | 1095 ± 40 | 0.8 ± 1.5 | 62.8 ± 1.0 | 0.999 |

TABLE B2-continued

Tube Current Modulation Model Parameters

| High BMI | AEC Off | 0.480 ± 0.001 | 0.997 | 1886 ± 66 | 0.7 ± 1.5 | 60.8 ± 1.6 | 0.999 |
|---|---|---|---|---|---|---|---|
| | Geometric | 0.436 ± 0.001 | 0.996 | 1773 ± 63 | 0.7 ± 1.4 | 55.4 ± 2.1 | 0.999 |
| | Global | 0.475 ± 0.001 | 0.997 | 1839 ± 64 | 0.7 ± 1.5 | 59.9 ± 1.6 | 0.999 |
| | CardiAEC | 0.479 ± 0.001 | 0.997 | 1874 ± 63 | 0.7 ± 1.5 | 61.9 ± 1.4 | 0.999 |

| | | $\mathcal{C}$ [mGy$^{1/2}$] | $R^2$ | $\mathcal{D}$ [mGy$^{Px}$] | | $P_x$ [-] | $X_o$ [-] | $R^2$ |
|---|---|---|---|---|---|---|---|---|
| Normal BMI | AEC Off | 1.058 ± 0.002 | 0.998 | 1.402 ± 0.115 | | 0.9 ± 1.8 | 0.172 ± 0.001 | 0.997 |
| | Geometric | 0.322 ± 0.001 | 1.000 | 0.182 ± 0.154 | | 1.0 ± 2.3 | 0.182 ± 0.002 | 0.731 |
| | Global | 0.630 ± 0.001 | 1.000 | 0.743 ± 0.122 | | 1.0 ± 2.0 | 0.173 ± 0.001 | 0.990 |
| | CardiAEC | 0.623 ± 0.001 | 0.999 | 0.983 ± 0.156 | | 1.1 ± 2.2 | 0.225 ± 0.001 | 0.991 |
| High BMI | AEC Off | 1.058 ± 0.002 | 0.998 | 1.402 ± 0.115 | | 0.9 ± 1.8 | 0.172 ± 0.001 | 0.997 |
| | Geometric | 1.066 ± 0.002 | 0.999 | 0.834 ± 0.069 | | 0.7 ± 1.4 | 0.193 ± 0.002 | 0.997 |
| | Global | 1.062 ± 0.002 | 0.998 | 1.505 ± 0.120 | | 0.9 ± 1.8 | 0.167 ± 0.001 | 0.998 |
| | CardiAEC | 1.107 ± 0.002 | 0.998 | 1.825 ± 0.138 | | 0.9 ± 1.9 | 0.135 ± 0.001 | 0.998 |

The rate of photon emission from the X-ray source is $$\lambda(\beta) = \frac{I_o \eta_s m(\beta)}{q_e}, \quad (C1)$$

where $I_o$ is the average tube current, $\eta_s$ is the source efficiency, $m(\beta)$ is the tube current modulation, and $q_e$ is the electron charge. The rate of photon survival at the detector, after passing through the beam-shaping filter and imaging target, is given by $$\phi(\gamma, \beta) = \frac{\lambda(\beta)\psi(\gamma)\exp(-g(\gamma, \beta))}{SDD^2}, \quad (C2)$$

where $\psi(\gamma)$ is the beam-shaping filter modulation, $g(\gamma,\beta)$ is the fan-beam transform of the imaging target given by (1), SDD is the source-detector distance, and an inverse-square law is assumed for intensity decay.

The discrete detectors and view angles are indexed by $\gamma_i$ and $\beta_j$, respectively, where $i \in \{1, \ldots, N_d\}$ and $j \in \{1, \ldots, N_p\}$, with $N_p$ denoting the number of projections acquired per gantry rotation. To simulate the stochastic effects of photon counting and generate realistic noise, the number of photons detected at $\gamma_i$ and $\beta_j$ is computed as a realization of the random variable $\hat{n}_{ij} \sim \text{Poisson}(n_{ij})$ where $$n_{ij} = \frac{\eta_d w SDD}{\Omega} \int_{\gamma_i - \frac{\Delta\gamma}{2}}^{\gamma_i + \frac{\Delta\gamma}{2}} \int_{\beta_j - \frac{\Delta\beta}{2}}^{\beta_j + \frac{\Delta\beta}{2}} \phi(\gamma, \beta) d\beta d\gamma, \quad (C3)$$

is the expected photon count, $\Delta\gamma = FA/N_d$ is the detector extent, $\Delta\beta = 2\pi/N_p$ is the gantry rotation increment, $w$ is the axial detector width, and $\Omega$ is the gantry rotation speed. Combining (C1)-(C3), we find that $$n_{ij} = C \int_{\gamma_i - \frac{\Delta\gamma}{2}}^{\gamma_i + \frac{\Delta\gamma}{2}} \int_{\beta_j - \frac{\Delta\beta}{2}}^{\beta_j + \frac{\Delta\beta}{2}} \psi(\gamma) m(\beta) \exp(-g(\gamma, \beta)) d\beta d\gamma, \quad (C4)$$

where we have defined the constant of proportionality $$C = \frac{I_o \eta_s \eta_d w}{q_e \Omega SDD}. \quad (C5)$$

In the absence of an imaging target, the detector would receive a calibrated number of photons given by $$c_{ij} = C \int_{\gamma_i - \frac{\Delta\gamma}{2}}^{\gamma_i + \frac{\Delta\gamma}{2}} \int_{\beta_j - \frac{\Delta\beta}{2}}^{\beta_j + \frac{\Delta\beta}{2}} \psi(\gamma) m(\beta) d\beta d\gamma. \quad (C6)$$

We evaluate (C4) and (C6) via numerical integration. The imaged sinogram is defined by $$\hat{g}_{ij} = -\log\left(\frac{\hat{n}_{ij}}{c_{ij}}\right) \quad (C7)$$

The sinogram error $\epsilon_{ij}$ is defined as the difference between the imaged and true sinogram and is computed by $$\epsilon_{ij} = \hat{g}_{ij} - g_{ij} \quad (C8)$$

where $g_{ij} = g(\gamma_i, \beta_j)$. For $\Delta\gamma, \Delta\beta \ll 1$, $$n_{ij} \approx C \Delta\gamma \Delta\beta \psi(\gamma) m(\beta) \exp(-g(\gamma,\beta)). \quad (C9)$$

We define sinogram noise as $$\sigma_{ij} = \sqrt{\text{Var}[\epsilon_{ij}]}. \quad (C10)$$

Using a Taylor series expansion approach to approximate moments of a function of a random variable $$\sigma_{ij} \approx \sqrt{\left(\frac{\partial}{\partial n}\left(-\log\left(\frac{n}{c_{ij}}\right) - g_{ij}\right)\bigg|_{n=n_{ij}}\right)^2 n_{ij}} \quad (C11)$$

which can be simplified as $$\sigma_{ij} \approx \frac{1}{\sqrt{n_{ij}}} \quad (C12)$$

We define noise index as $$NI_{ij} = \frac{1}{\sqrt{n_{ij}}}, \quad (C13)$$

we see that $$\sigma_{ij} \approx NI_{ij} \propto \frac{1}{\sqrt{C}}. \quad (C14)$$

Therefore, we expect $C$ to be in an inverse square root relationship with noise.

Conventionally, the "bowtie" design for a beam-shaping filter attempts to compensate for attenuation variation in a circular cylinder of diameter D, concentric with the scanner isocenter, and materially homogeneous with a linear attenuation coefficient $\mu_p$. The filter modulation satisfying these criteria is $$\psi_{bt}(\gamma) = \begin{cases} \exp\left(D\mu_p \sqrt{1 - \left(\frac{2SAD}{D}\sin\gamma\right)^2}\right) & |\gamma| \leq \gamma_{bt}, \\ \psi_o & |\gamma| > \gamma_{bt}, \end{cases} \quad (D1)$$

where $$\gamma_{bt} = \sin^{-1}\left(\frac{D}{2SAD}\sqrt{1 - \left(\frac{\log(\psi_{min})}{D\mu_p}\right)^2}\right) \quad (D2)$$

is the angular cutoff based on minimum allowable fluence $\psi_{min}$.

The CardiaBeam filter reduces X-ray fluence to a small, albeit nonzero value for rays outside of an ROI of diameter d. The filter modulation is $$\psi_{cb}(\gamma) = \begin{cases} 1 & |\gamma| \leq \gamma_{ROI}, \\ \psi_{min} & |\gamma| > \gamma_{ROI}, \end{cases} \quad (D3)$$

where $\gamma_{ROI} = \sin^{-1}(d/2SAD)$ and $\psi_{min} = 1 - 1/f_o$ where $f_o$ is a modulation factor. Note that the static beam-shaping filter according to the disclosed technology (CardiaBeam) can also have other forms and/or shapes of the $\psi_{cb}(\gamma)$ dependence. The common feature of the beam-shaping filters according to the disclosed technology is that they provide the highest fluence of X-ray radiation from an X-ray source of a CT scanner in the ROI and simultaneously maintain a level of fluence of the X-ray radiation on the areas of the imaging target located outside the ROI at a level above a certain predetermined fluence threshold value which allows avoiding artifacts related to the interior tomography problem.

Geometrically, the human chest cavity is dominated by asymmetry between the anteroposterior and lateral dimensions. Using an elliptical phantom of homogeneous, tissue-equivalent attenuation $\mu_p$ and semimajor and semiminor axes $d_{lt}$ and $d_{ap}$, respectively, the compensating tube current modulation is $$m_{geo}(\beta) = c_{geo}\exp\left(\frac{2d_{ap}\mu_p}{\sqrt{1 - \left(1 - \frac{d_{ap}^2}{d_{lt}^2}\right)\sin^2\beta}}\right), \quad (E1)$$

where $c_{geo}$ is a normalization constant to ensure $$\frac{1}{2\pi}\int_0^{2\pi} m(\beta)d\beta = 1.$$

This is the "Geometric" modulation scheme.
Using (C13), $$NI_{ij} \propto (m(\beta_j)\psi(\gamma_i)\exp(-g(\gamma_i, \beta_j)))^{-\frac{1}{2}}. \quad (E2)$$

We define a region on the detector as $\mathcal{G}(\beta)$. The average noise index in this region is given by $$\overline{NI}(\beta) \propto \int_{\mathcal{G}(\beta)} (m(\beta)\psi(\gamma)\exp(-g(\gamma, \beta)))^{-\frac{1}{2}} d\gamma. \quad (E3)$$

To equalize the average noise index in $\mathcal{G}(\beta)$ overall view angles, we set $\overline{NI}(\beta)$ to a constant and solve for the resulting modulation function $$m_{NI}(\beta) = c_{NI}\left(\int_{\mathcal{G}(\beta)} (\psi(\gamma)\exp(-g(\gamma, \beta)))^{-\frac{1}{2}} d\gamma\right)^2, \quad (E4)$$

$c_{NI}$ is a normalization constant to ensure $$\frac{1}{2\pi}\int_0^{2\pi} m(\beta)d\beta = 1.$$

The probability density function of the scaled Student's t distribution is $$P(\epsilon) = \frac{\Gamma\left(\frac{1}{2\chi} + \frac{1}{2}\right)}{\sigma\sqrt{\frac{\pi s^2}{\chi}}\Gamma\left(\frac{1}{2\chi}\right)}\left(1 + \frac{\chi\epsilon^2}{s^2}\right)^{-\frac{1}{2\chi}-\frac{1}{2}} \quad (F1)$$

where $\Gamma(\bullet)$ is the Gamma function, s is a scale parameter, and $\chi$ is a parameter quantifying the prevalence of outliers.

While cardiac CT has a clear clinical role in the evaluation of coronary artery disease (CAD) and assessment of coronary artery calcium (CAC), the use of ionizing radiation currently limits its clinical use. To test whether a reduced scan field of view (FOV) can be achieved by placing the heart at the scanner isocenter and the extent to which this can lead to dose reduction in the setting of coronary artery calcium (CAC) scoring without reducing CAC scoring accuracy, the location of 38,184 calcium lesions from 3,151 studies with calcium scores >0 in the Multi-Ethnic Study of Atherosclerosis (MESA) were utilized to define patient positioning strategies and assess their impact on CAC scoring accuracy. Specifically, the scan FOV diameter needed for accurate CAC scoring between body-centered positioning and demographic model-based, heart-centered positioning according to the disclosed technology were compared. In a validation cohort of 118 individuals (81 with CAC>0), the resulting CAC accuracy of reduced scan FOV imaging and the extent of dose reduction via changes to the beam-shaping filter was assessed.

Heart-centering with a demographic positioning model according to an example embodiment of the disclosed technology reduced the required scan FOV 25.7% relative to body-centered positioning while preserving CAC scoring accuracy (0.82% risk reclassification rate). In our validation cohort, a median dose reduction of 26.9% (25-75th percentile: 21.6 to 29.8%) was achieved via demographic-based, heart-centered positioning with tailored beam-shaping filtration according to an example implementation of the disclosed technology without any calcium risk reclassification. Heart-centered, demographic model-based patient positioning according to the disclosed technology enables a significant CT radiation dose reduction while maintaining diagnostic accuracy.

Cardiac CT plays a critical role in the non-invasive assessment of cardiovascular disease. For example, coronary artery calcium (CAC) improves risk prediction beyond traditional risk factors and CT coronary angiography (CTCA) is a powerful diagnostic and prognostic tool for coronary artery disease (CAD). However, the use of ionizing radiation has raised concern about accumulation of radiation dose in the population. As a result, despite its potential benefits, widespread use of cardiac CT is limited by radiation risk concerns. For example, CAC screening is currently recommended only in individuals at intermediate 10-year risk of CAD if traditional tools leave treatment uncertain.

To maximize the risk-benefit ratio of CT imaging, dose-reduction techniques are important. Generally, scan protocols adhere to the "as-low-as-reasonably-acceptable" (ALARA) principle where dose is reduced by limiting image quality to the minimum needed for the diagnostic task. To further reduce dose, for example, patients can be placed at the center of the scanner and asked to raise their arms to reduce their cross-sectional extent. In addition, beam-shaping "bow-tie" filters can be designed to equalize X-ray photon counts across detectors. By decreasing X-ray fluence to peripheral, less attenuating regions of the body, these filters reduce dose and equalize image quality throughout the field-of-view (FOV). Incorrect patient positioning is known to increase radiation dose. Automated, camera-based patient position detection and moving tables can address this issue.

The design of currently used beam-shaping filters and body-centered patient positioning strategy does not take into account the fact that clinical interest in cardiac imaging is limited to the heart—an off-center subsection of the larger chest cavity. While the entire patient cross-section must be imaged to avoid limited FOV artifacts, significant dose reductions can be achieved through technology disclosed herein by limiting higher X-ray fluence to a subregion of the FOV, positioning the region of interest at the scanner isocenter and using an appropriate beam-shaping filter. This necessitates determination of the center and diameter of the cardiac region of interest prior to scanning.

We evaluate the extent to which heart-centered scanning can reduce the imaging diameter required for accurate CAC scoring and, when combined with tailoring of the beam-shaping filter, can reduce dose while maintaining CAC accuracy. To do so, we utilize CAC lesion locations identified in MESA to determine the size and location of the region needed for heart imaging and generate a demographic-based patient positioning model. Then, in a validation cohort of CAC scoring scans, we assess the impact of heart-centered positioning on CAC scoring accuracy and dose reduction via simulation.

The Multi-Ethnic Study of Atherosclerosis (MESA) studied subclinical atherosclerosis in a diverse cohort of individuals without a history of clinically recognized cardiovascular disease and its study design has been published previously. The study was approved by the institutional review committee at each participating institution and all subjects gave informed consent.

As part of an approved substudy, calcium scans of 3,151 MESA participants with CAC>0 on Exam 1 were previously annotated to evaluate the effect of calcium lesion density. The location of 38,184 calcium lesions were annotated with spatial information (slice number and spatial position in the axial plane) as well as anatomical information (corresponding coronary vessel). Relevant demographic information for this MESA cohort is shown in Table II.

TABLE II

Cohort Demographics

|  | MESA All N = 6814 | CAC > 0 N = 3151 | Validation Cohort All N = 118 | CAC > 0 N = 81 |
|---|---|---|---|---|
| Age (years) | 62 (53-70) | 67 (60-74) | 66 (57-70) | 67 (59-71) |
| Gender (female) | 3601 (53%) | 1319 (42%) | 65 (55%) | 41 (51%) |
| BMI (kg/m$^2$) | 28 (25-31) | 28 (25-31) | 26 (23-30) | 26 (24-31) |
| Race |  |  |  |  |
| White | 2622 (38%) | 1384 (44%) | 93 (79%) | 68 (84%) |
| Chinese | 804 (12%) | 385 (12%) | 13 (11%) | 8 (10%) |
| Black | 1892 (28%) | 747 (24%) | 1 (1%) | 1 (1%) |
| Hispanic | 1496 (22%) | 635 (20%) | 11 (9%) | 4 (5%) |
| CAC |  |  |  |  |
| =0 | 3663 (54%) |  | 37 (31%) |  |
| >0 | 3151 (46%) |  | 81 (69%) |  |
| 1-100 |  | 1827 (58%) |  | 34 (42%) |
| 100-400 |  | 962 (31%) |  | 26 (32%) |
| 400+ |  | 362 (11%) |  | 21 (26%) |

Relative to the MESA cohort, our validation cohort was similar in age and gender but had significantly lower BMI, included more White participants, and had more coronary artery calcium. In Table II, continuous variables are reported as median with the $1^{st}$ to $3^{rd}$ quartile range. Categorical values are shown as counts with percentages in parentheses.

Figure 11A:
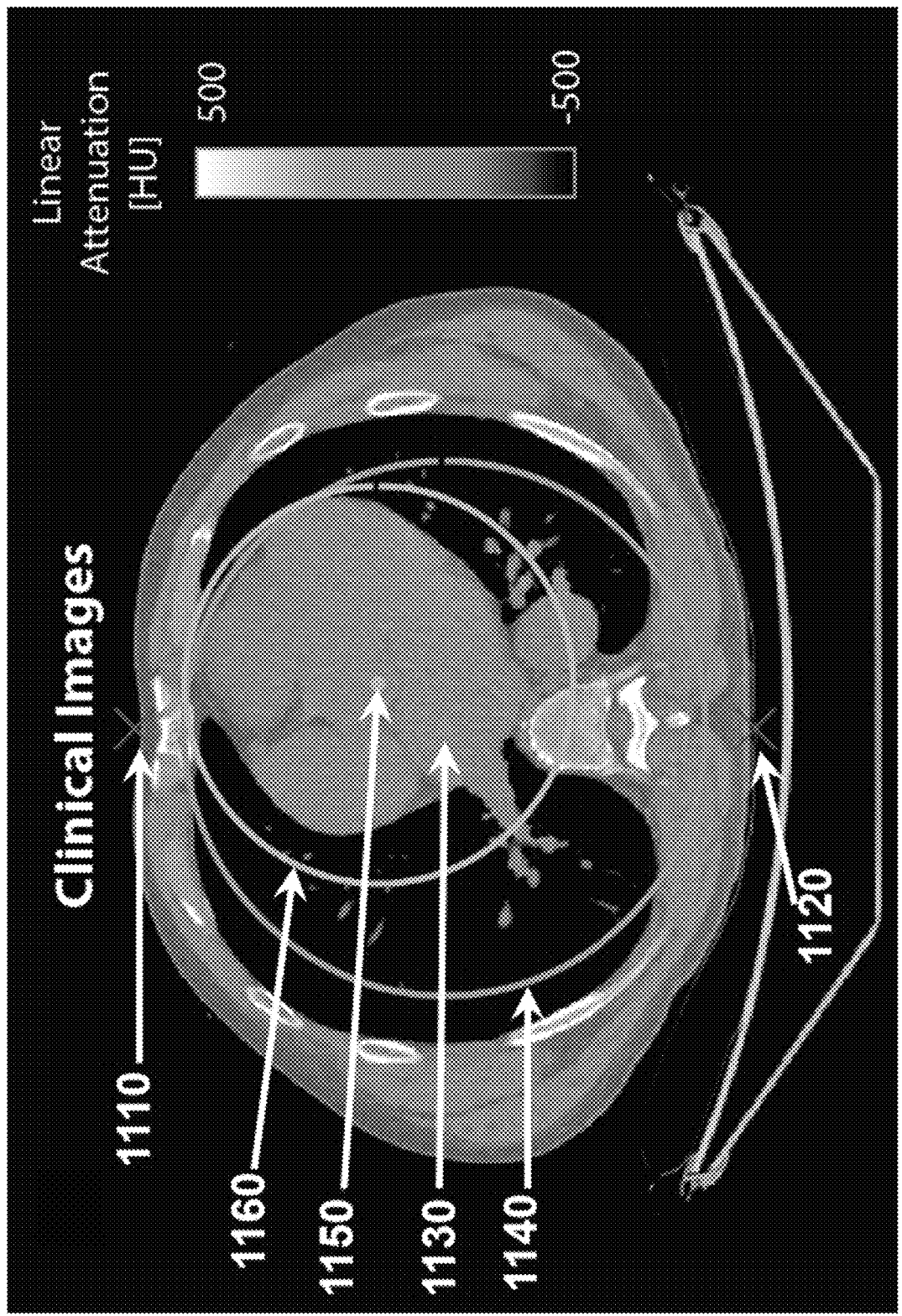
FIGS. 11A-11D illustrate an image analysis pipeline according to an example embodiment of the disclosed technology.

To standardize lesion location, a common anatomical origin was defined for each participant. First, images were semantically segmented using a deep learning-enabled neural network. From these segmentations, the participant's midline was defined via the centroid of the spine label. The posterior skin boundary at the midline was defined as the origin (FIG. 11A, lower 'x' mark 1120). This location was chosen because it could be identified on scout imaging. The location of each calcium lesion was measured relative to this origin. For each of the four vessels (left main, left anterior descending, left circumflex, and right coronary), a distribution of lesion positions was generated.

Figure 11B:
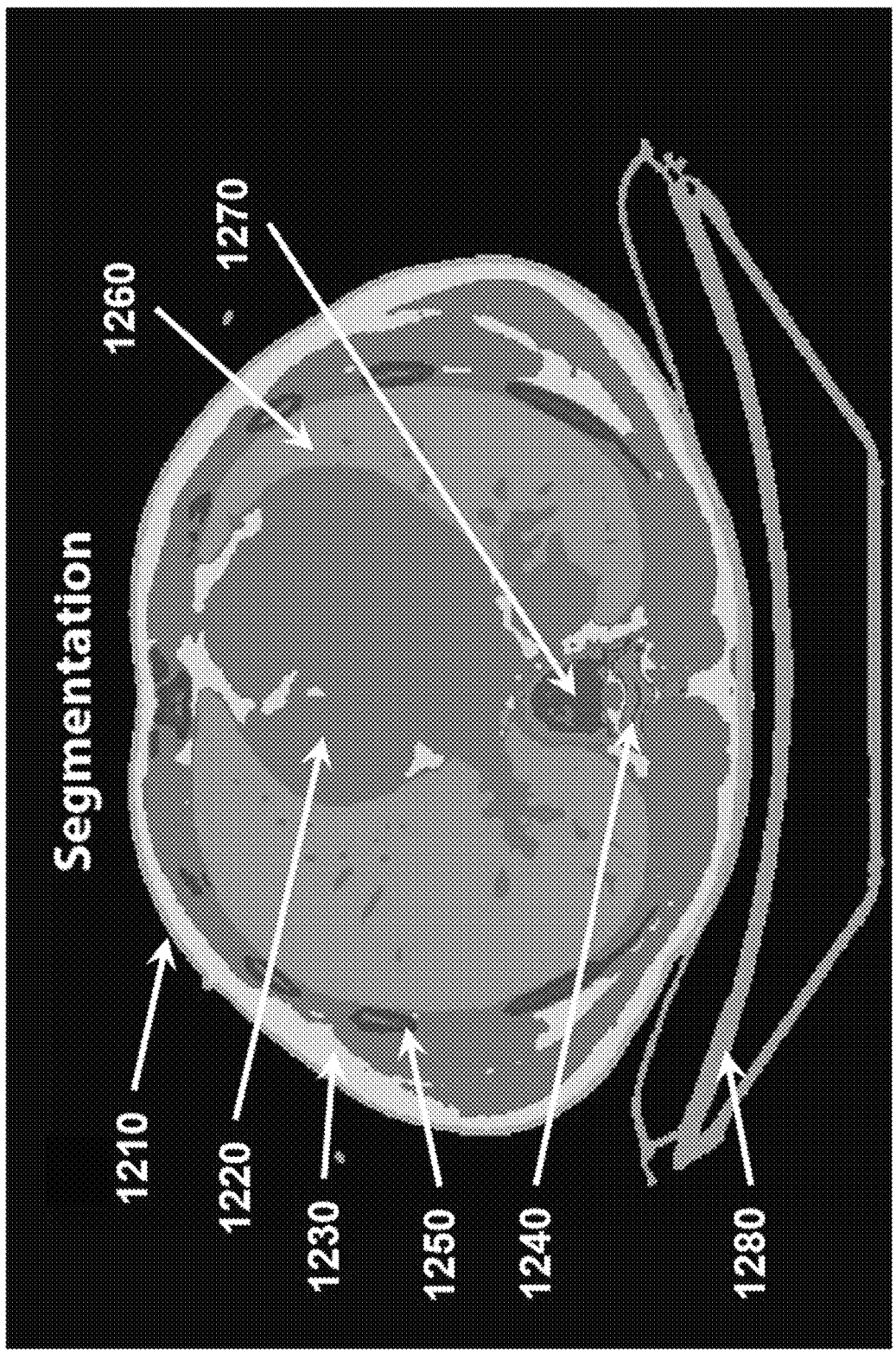
Figure 11C:
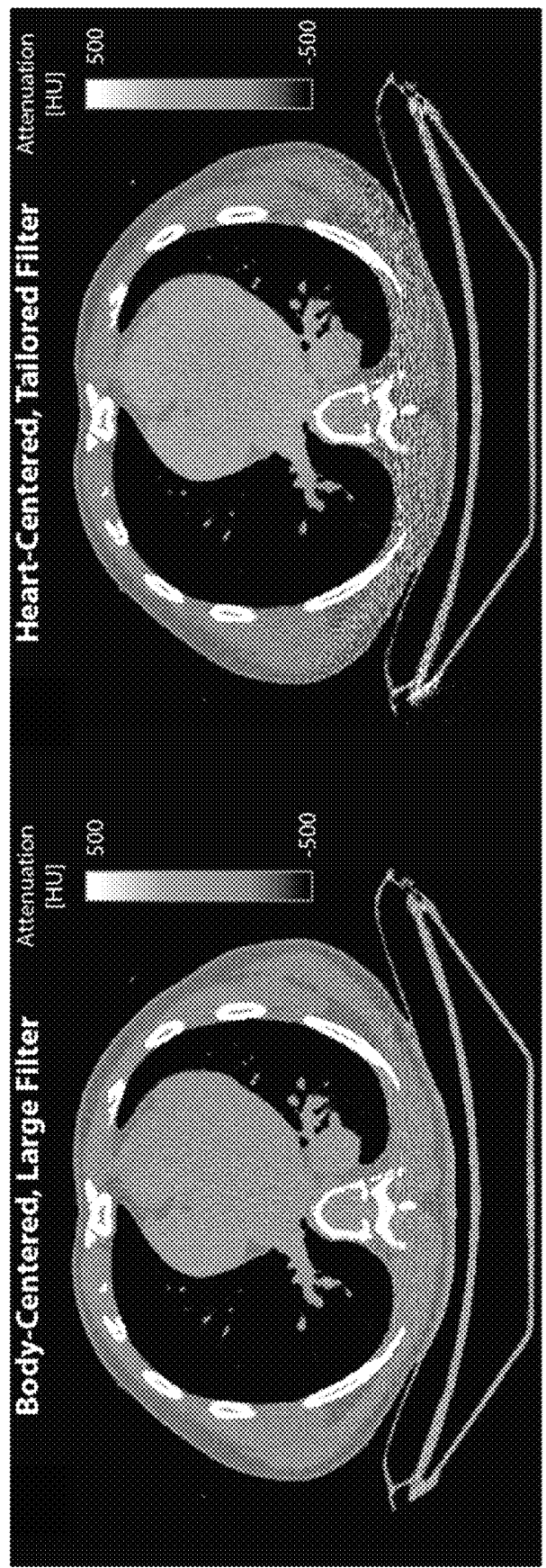
Figure 11D:
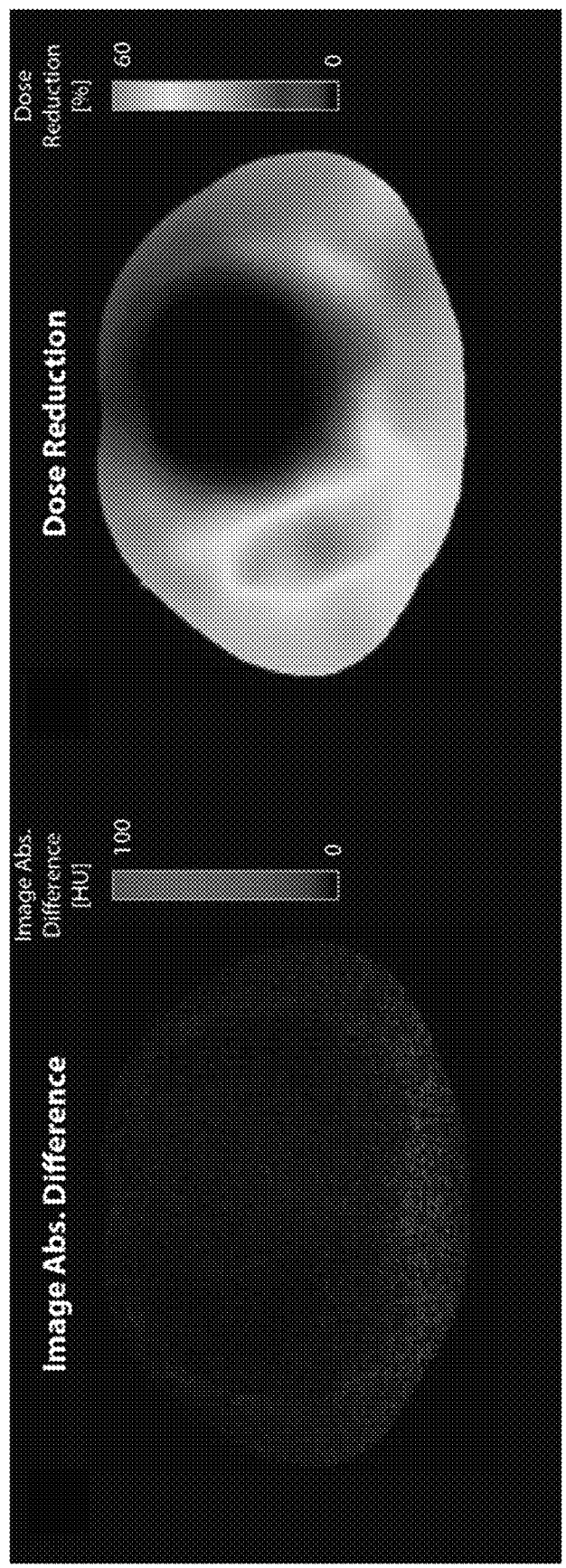

FIGS. 11A-11D illustrate an image analysis pipeline according to an example embodiment of the disclosed technology. Full field of view (500 mm) images (FIG. 11A) are analyzed to define anterior and posterior skin extent at patient midline (marked by the 'x' marks 1110 and 1120 in FIG. 11A, respectively). Body center (1130) and heart center (1150) and their respective scan fields of view (SFOV) 1140 and 1160 are depicted in the central slice in FIG. 11A (window level (WL)/width (WW)=0/1000 HU) Automated semantic segmentation via neural network is used to identify tissue types and generate voxelized phantoms, as shown in FIG. 11B (1210: skin, 1220: muscle/blood, 1230: fat, 1240: spine, 1250: bone, 1260: lung, 1270: bone marrow, 1280: couch). FIG. 11C shows reconstructed images (WL/WW=0/1000 HU) generated via a simulation for a conventional body-centered Large filter (on the theft side of FIG. 11C) and a heart-centered, tailored filter according to an embodiment of the disclosed technology (on the right side of FIG. 11C) for comparison. FIG. 11D shows an absolute difference image (left; WL/WW=50/50 HU) and a simulated dose reduction map (right; WL/WW=30/30%) and illustrates that high image quality is achieved using the tailored approach according to the disclosed technology with significant dose reductions particularly in the lateral and posterior portions.

Patient-specific coronary vessel localization was defined by a linear regression model with demographic inputs (age, sex, BMI, and race/ethnicity). The axial vessel positions were denoted $p_v=(x_v,y_v)$, where v denotes a vessel index (1 to 4). Heart-centered position in the axial plane was found by computing the center of the smallest circle (center 1150 of the circle 1160 in FIG. 11A) that bounds the predicted positions of the four coronary arteries. These coordinates were denoted $c_{heart}=(x_{heart},y_{heart})$.

For comparison, a body-centered positioning approach was evaluated. The center position was defined as the midpoint between the anterior and posterior skin boundaries at the midline. This position was denoted $c_{body}=(x_{body},y_{body})$ and is shown as the dot 1130 and circle 1140 in FIG. 11A.

To assess the effect of heart centering, lesions were re-positioned according to each positioning strategy and the accuracy of CAC scoring as a function of scan FOV was measured. Accuracy was quantified according to three metrics: risk reclassification rate (RRR), Lin's correspondence correlation coefficient (CCC) of log(Agatston+1), and the lesion miss rate (LMR). Risk classification was based on binning Agatston scores into the following categories: CAC=0, 1-100, 100-400, and 400+.

A validation cohort of 156 consecutive calcium scans acquired on a single CT scanner (Revolution, GE Healthcare, Chicago, IL) with corresponding demographic information were identified with IRB-approved waiver of informed consent to validate the MESA-derived heart-centering approaches and quantify dose reduction. Images were acquired using the Body filter with ECG gating. 118 individuals met the inclusion criteria of having 1) a full (500 mm diameter) image reconstruction with the entire chest cross-section inside the image (for accurate dose estimation), 2) no implanted metal devices which precluded semantic segmentation and dose estimation, and 3) sufficient image quality for calcium scoring. Relevant demographic information is shown in Table II Notably, 81 (69%) individuals had Agatston CAC score >0.

A certified CTCA imaging cardiologist annotated the calcium scans to generate calcium lesion location data in the same manner as in the MESA substudy. As with the MESA data, individuals were first aligned using the common origin (described above) to account for variation in positioning by the technician. Then, each individual was repositioned according to either heart- or body-centering. Heart-centering was evaluated both in terms of calcium scoring accuracy, using the metrics described above, as well as image quality and radiation dose, as described below, via simulation.

Simulation was used to evaluate changes in radiation dose and image quality due to heart-centered positioning and the use of different beam-shaping filters. The previously-described heart-centered positioning approach was combined with three different beam-shaping filters.

For beam-shaping filters, two conventional filter profiles were modeled after existing "bow-tie" filters on the GE Revolution scanner, hereafter referred to as "Large" and "Small". Additionally, a tailored beam-shaping filter profile was designed, the diameter of which is based on the MESA lesion analysis for demographic model-based heart-centered positioning. The performance of each scan mode was compared to a baseline approach using body-centered positioning and the "Large" filter.

Figure 12:
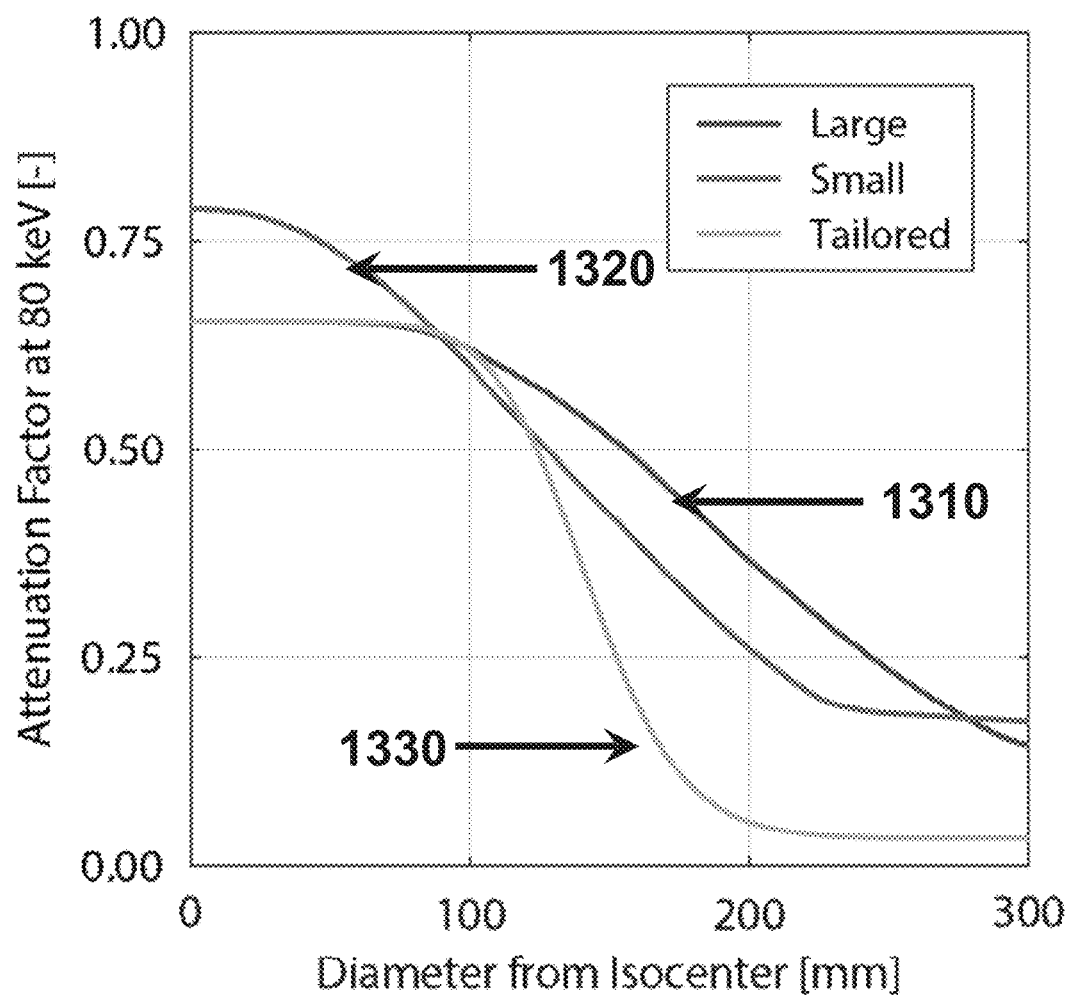
FIG. 12 shows attenuation profiles of several example beam-shaping filters.

FIG. 12 shows the attenuation profiles of the filters under consideration. In FIG. 12, attenuation profiles for filters available on the GE Revolution scanner are shown by the curves 1310 (for the Large filter) and 1320 (for the Small filter). Attenuation profile for a filter according to an example embodiment of the disclosed technology is shown by the curve 1330 in FIG. 12. As shown in FIG. 12, that filter has a more tailored attenuation profile based on the heart-centered diameter (168 mm) identified in the MESA cohort, as compared to the conventional Large and Small filters. Here, we employed a conservative design where the relative attenuation is 20 times higher at 80 keV in the peripheral regions than along the center ray, whereas the conventional filters opt for approximately 4 times attenuation in the periphery. The filter profile is designed to deliver the highest X-ray fluence to a 168 mm diameter circular region centered at the isocenter.

The absorption of X-ray radiation was simulated using voxelized representations of anatomies obtained from the semantic segmentations described above. Density-weighted dose averages were then computed in four anatomical regions of interest: the entire thorax, the lungs, the spine, and the skin.

In addition to radiation dose, repositioning changes the X-ray fluence through the heart region of interest and therefore the noise in the reconstructed image. The imaging process was simulated in the central slice, and Poisson noise was incorporated at varying fluence levels to generate sinograms with various noise levels as well as at a noiseless condition. The relationship between X-ray tube current I and noise $e^2$ was used to the effects of scanning mode on image quality.

Since the scan mode impacts both image noise and dose, we compare scan modes using both constant fluence and constant image noise conditions.

Measures were tested for normality using the Shapiro-Wilks test. Unless otherwise specified, normally-distributed variables are reported as mean±0.674* standard deviation (to match quartiles of the normal distribution). Measures where the normality hypothesis was rejected are reported as median with first and third quartiles (Q1 and Q3, respectively). Student's t-test and ANOVA were used to assess statistical significance for normally-distributed variables while Wilcoxon rank-sum and Kruskal-Wallis were used to assess statistical significance for non-normally distributed variables, all at significance level p=0.05.

Rate metrics (RRR and LMR) observed in the validation cohort were assessed using post-hoc power analysis. Confidence bounds for the observed MESA values were determined for 80% power and significance level 0.05, and accounting for the size of the validation cohort. Validation rate metrics observed outside of these bounds permitted rejection of the null hypothesis that the validation data were the same as those from MESA.

Multivariate LASSO linear regression of dose reduction was performed to identify associations between dose reduction and image acquisition parameters (bowtie filter and positioning approach) and demographics.

In the MESA population, the body center position was found to be 127 mm (Q1-Q3: 117 to 137 mm) anterior relative to the posterior midline location.

Patient-specific demographic modeling of the heart position led to a 159 mm (Q1-Q3: 148 to 169 mm) anterior and 12 mm (Q1-Q3: 9 to 15 mm) leftward shift. Four demographic variables (age, sex, BMI, and race/ethnicity) were utilized and each was a significant ($p<0.05$) predictor in at least one vessel/coordinate model.

Figure 13:
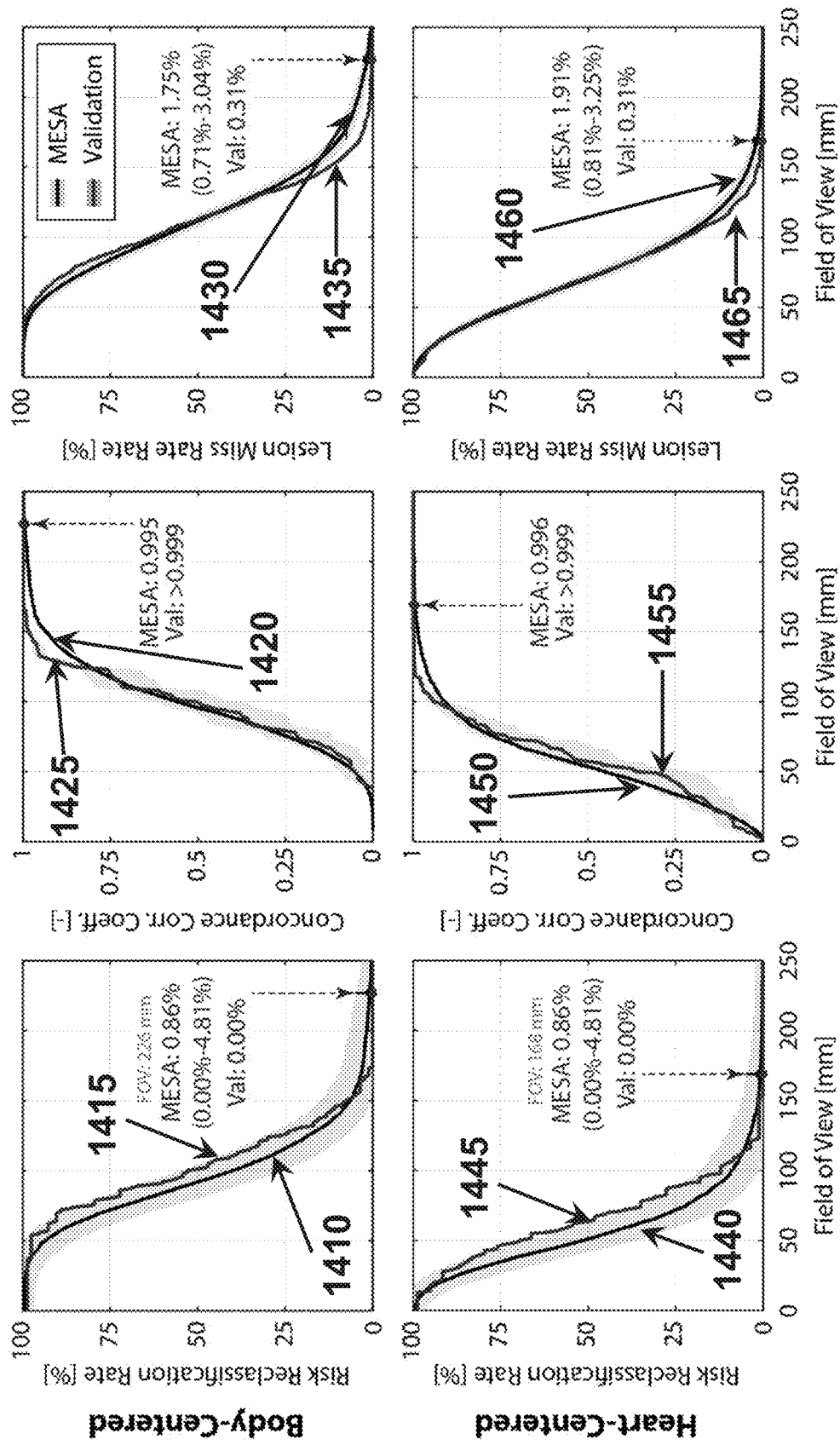
FIG. 13 illustrates that heart-centered positioning according to the disclosed technology decreases the scan field-of-view (FOV) needed for high accuracy coronary artery calcium (CAC) scoring.

Heart-centered positioning according to the disclosed technology decreased the scan FOV needed for high accuracy CAC scoring (Table III and FIG. 13). FIG. 13 shows that heart-centering according to the disclosed technology correctly captures calcium lesions and permits accurate Agatston scoring at reduced scan field-of-view (SFOV). Heart centering (top row) reduces the FOV relative to body-centering (bottom row) while maintaining high calcium score risk classification accuracy (left), high concordance correlation coefficient (middle), and low lesion miss rate (right). Curves 1410, 1420, 1430, 1440, 1450, and 1460 in FIG. 13 correspond to MESA data. Curves 1415, 1425, 1435, 1445, 1455, and 1465 in FIG. 13 correspond to the resulting performance in the validation cohort. Confidence bounds for RRR and LMR were computed using post-hoc power analysis based observed MESA values, 80% power and significance level 0.05, and accounting for the size of the validation cohort (N=81 individuals and N=979 lesions, respectively).

Repeat calcium scoring in MESA had an 8.2% risk reclassification rate (RRR). For a RRR of 0.82% (ten-times lower than repeat scanning), demographic-based heart centering reduced the required SFOV 25.7%. In the MESA cohort, RRR=0.82% was associated with a very small number of missed lesions (1.91%) and very high concordance correlation coefficient (0.996) for Agatston scoring.

TABLE III

Heart centering enables assessment within a reduced SFOV with high calcium scoring accuracy as assessed in both the MESA and validation cohorts.

|  | Body-Centered | Heart-Centered |
|---|---|---|
| Risk Reclassification Rate (%) | | |
| MESA | 0.86 (0.00-4.87) | 0.86 (0.00-4.87) |
| Validation | 0.00 | 0.00 |
| Concordance Correlation Coefficient | | |
| MESA | 0.995 | 0.996 |
| Validation | >0.999 | >0.999 |
| Lesion Miss Rate (%) | | |
| MESA | 1.75 (0.71-3.04) | 1.91 (0.81-3.25) |
| Validation | 0.31* | 0.31* |

In Table III, RRR: Risk Reclassification Rate; CCC: Concordance Correlation Coefficient for log(Agatston+1) scoring; LMR: Lesion Miss Rate. Confidence bounds for RRR and LMR were computed using post-hoc power analysis based observed MESA values, 80% power and significance level 0.05, and accounting for the size of the validation cohort (N=81 individuals and N=979 lesions, respectively). Asterisks indicate where validation performance was better than the predicted confidence bound.

Positioning and calcium scoring accuracy (with MESA-derived SFOV diameters) were validated in 120 individuals who underwent calcium scanning. As shown in Table II, the validation cohort was of similar age (All: $p=0.07$, CAC>0: $p=0.28$) and gender (All: $p=0.63$, CAC>0: $p=0.11$) as the MESA cohort but had significantly lower BMI (All: $p<0.01$, CAC>0: $p=0.05$), lower prevalence of Black and Hispanic subjects (All: $p<0.01$, CAC>0: $p<0.01$), and higher CAC scores (higher percentage of individuals with CAC>0 as well as scores >400, $p<0.01$).

Body centering in our validation cohort was found to be 120 mm (Q1-Q3: 110 to 131 mm) anterior relative to the posterior midline location. Patient-specific demographic-based positioning identified a 156 mm (Q1-Q3: 145 to 164 mm) anterior and 12 mm (Q1-Q3: 10 to 14 mm) leftward shift.

In both patient positioning approaches, we observed perfect calcium risk classification (RRR=0.00%), high calcium scoring accuracy (CCC>0.999), and lesion miss rates below the range predicted by MESA. This confirms the ability of demographic model-based positioning according to the disclosed technology to reduce the FOV (e.g., by 25.7%) relative to body centering without the loss of calcium scoring accuracy.

Figure 14:
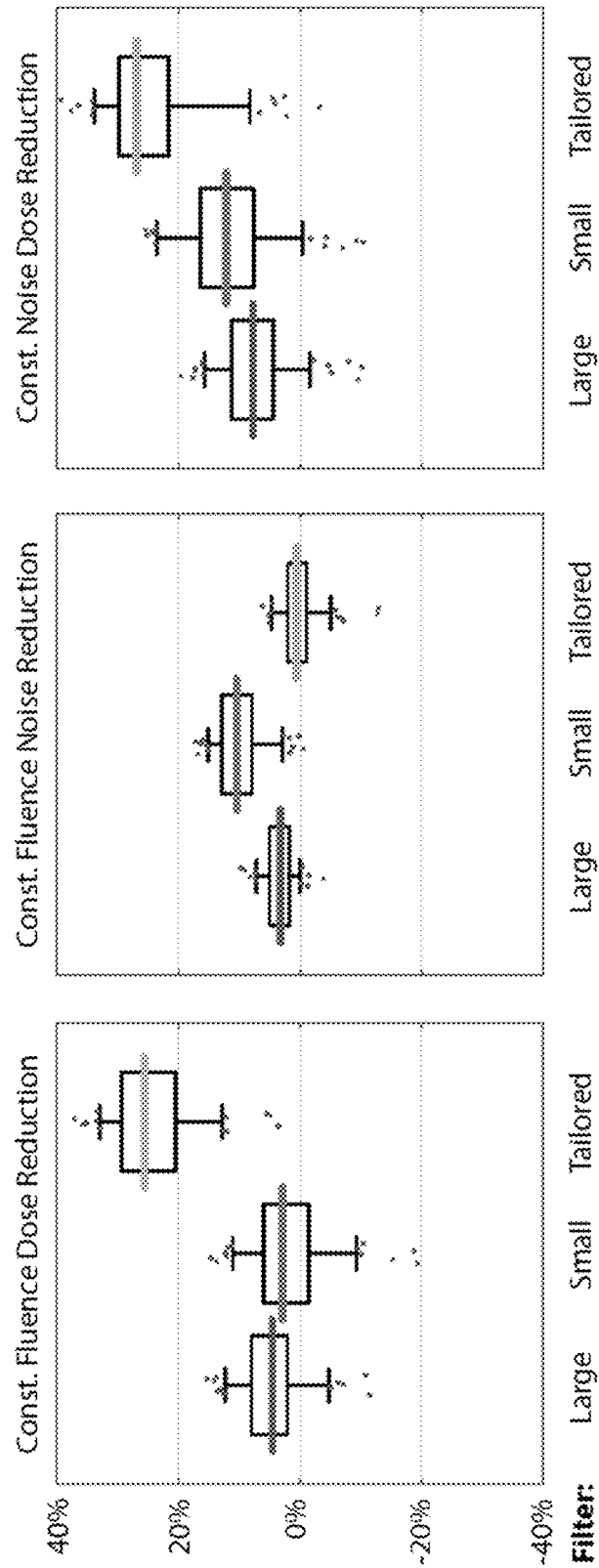
FIG. 14 shows example distributions of simulation-predicted dose reductions for heart centered positioning with different beam-shaping filters.

The distributions of simulation-predicted dose reductions (relative to body-centered imaging with the Large filter) for heart centered positioning with different beam-shaping filters are shown in FIG. 14. In FIG. 14, horizontal lines indicate median value, black box indicates first and third quartiles, whiskers indicated 5th and 95th percentiles. Gray circles indicate additional data beyond the 5th and 95th percentiles. Summary statistics are shown in Table IV. In Table IV, median values are shown with ranges from 1st to 3rd quartiles. Heart centering with tailored filtering according to an example embodiment of the disclosed technology reduced dose 26.9% (Q1-Q3: 21.5 to 29.8%). The improvement is primarily due to dose reduction (25.5%, Q1-Q3: 20.4 to 29.6%) with a small improvement in image noise (0.6%, Q1-Q3: −1.2 to 2.0%). Additional reductions can be achieved if the scan FOV were adjusted for each individual.

TABLE IV

Heart-centering enabled tailoring of the acquisition enables a reduction in dose.

|  | Large | Small | Tailored |
|---|---|---|---|
| Constant Fluence | 4.6 | 2.9 | 25.5 |
| Dose Reduction (%) | (2.0-8.0) | (−1.5-6.0) | (20.5-29.4) |
| Image Noise Reduction (%) | 3.2 | 10.4 | 0.6 |
|  | (1.7-5.1) | (7.9-12.8) | (−1.0-2.0) |
| Constant Image Noise | 7.7 | 12.2 | 26.9 |
| Dose Reduction (%) | (4.4-11.3) | (7.5-16.4) | (21.6-29.8) |

The use of the Small filter (currently available on the GE scanner) reduced dose 12.1% (Q1-Q3: 7.4 to 16.3%) with heart centering. This stems from a modest reduction in dose (2.9%, Q1-Q3: −1.5 to 6.3%) but larger improvement in image noise (10.4%, Q1-Q3: 7.6 to 12.8%).

Reductions in dose or image noise were not significantly different between individuals with CAC=0 and those with CAC>0 ($p>0.05$ for all conditions).

The positioning model, Small and tailored beam-shaping filter, BMI, sex, and Agatston score were significantly associated with dose reduction (overall model adjusted R2=0.72). The demographic-based heart centering ($\beta$=7.4, CI: 5.7 to 9.2, p<0.001), small filter ($\beta$=4.2, CI: 2.4 to 6.0, p<0.001), tailored filter according to the disclosed technology ($\beta$=17.1, CI: 15.3 to 18.8, p<0.001), BMI ($\beta$=0.3, CI: 0.2 to 0.4, p<0.001), and male sex ($\beta$=2.9, CI: 1.6 to 4.1, p<0.001) were associated with increased dose reduction while log(Agatston+1) was associated with decreased dose reduction ($\beta$=−0.6, CI: −0.9. to −0.2, p<0.001).

Tailored beam filtration according to an implementation of the disclosed technology enabled by heart centering reduced dose 35.7% to the spine (Q1-Q3: 30.4 to 41.2%), 26.4% to the lungs (Q1-Q3: 21.9-31.1%), and 9.8% to the skin (Q1-Q3: 1.8 to 14.8%), see Table V. Use of the Small filter led to reductions in lung and spine dose (16.3 and 31.1%, respectively) but an increase in skin dose (17.2%, Q1-Q3: 12.4 to 22.9%).

TABLE V

Dose reduction shows regional variations.

| Dose Reduction (%) | Large | Small | Tailored |
| --- | --- | --- | --- |
| Thorax | 7.7 | 12.2 | 26.9 |
|  | (4.4-11.3) | (7.5-16.4) | (21.6-29.8) |
| Lungs | 7.7 | 16.3 | 26.4 |
|  | (3.9-10.7) | (11.4-19.3) | (22.1-31.3) |
| Spine | 25.6 | 31.1 | 35.7 |
|  | (18.2-32.9) | (25.8-36.6) | (30.1-41.3) |
| Skin | −28.6 | −17.2 | 9.8 |
|  | (−33.6-−23.6) | (−22.9-−12.4) | (1.9-14.8) |

In Table V, median values shown with ranges from 1st to 3rd quartiles. Heart centering with tailored beam-shaping filtration according to the disclosed technology decreases simulation-predicted dose to all four anatomical regions. The Small filter reduces dose to the lungs and spine but leads to an increased skin dose.

Large and diverse MESA study population was used to define the location and diameter of the heart region based on the distribution of CAC lesions. We show that we can predict the center of the heart region in a patient-specific fashion, using patient's demographic information. Doing so enabled a reduction (e.g., by 25.7%) of the scan FOV without loss of calcium scoring accuracy.

Several CT imaging protocols can benefit from the heart centering approach according to the disclosed technology. The region we identified is likely very close to the region of interest in CTCA. Additionally, other cardiac applications such as the evaluation for transcatheter aortic valve replacement could benefit from a tailored acquisition according to the disclosed technology with slight modification of the region of interest. In addition, the congenital and pediatric cardiac population often undergo repeated CT imaging for diagnosis and follow-up and would benefit greatly from dose reduction. More generally, non-cardiac applications can also benefit from the disclosed technology if a reliable method is available to identify and define the region of imaging interest.

In some applications, cardiac scans are performed longitudinally. Prior scans can be used to further tailor the imaging approach according to the technology disclosed in this patent document. For example, imaging of a specific coronary vessel (to assess stent patency, for example), can be performed with a scan FOV even more limited than the one used to assess the entire heart. Realizing additional reductions would require a filter according to the disclosed technology that can adapt to the desired scan FOV.

According to an embodiment of the disclosed technology, where calcium lesions are (or, generally, where a ROI is) is determined or predicted relative to anatomical landmarks which could be identified and localized with respect to the scanner coordinates, for example. Specifically, we chose the posterior skin extent as an anteroposterior landmark because it corresponds to where the patient meets the table surface. We chose the spine as a lateral landmark as it can be readily identified on scout imaging, or in some cases visually. These landmarks can be identified, for example, by neural network segmentation of scan images. Patient-specific predictions of ROI position can be also made directly from scout imaging, for example.

Technology disclosed in this patent document can introduce an additional step in the data acquisition process of CT scanners. While moving the patient anterior/posterior after they have been laid on the scanner can be performed using the table, lateral movement is not currently available on most commercial scanners. In lieu of moving the table, the lateral offset could be applied when the patient lays down as the offset is based on demographics, according to the disclosed technology, and can be determined prior to scanning when the midline is estimated externally.

Figure 15:
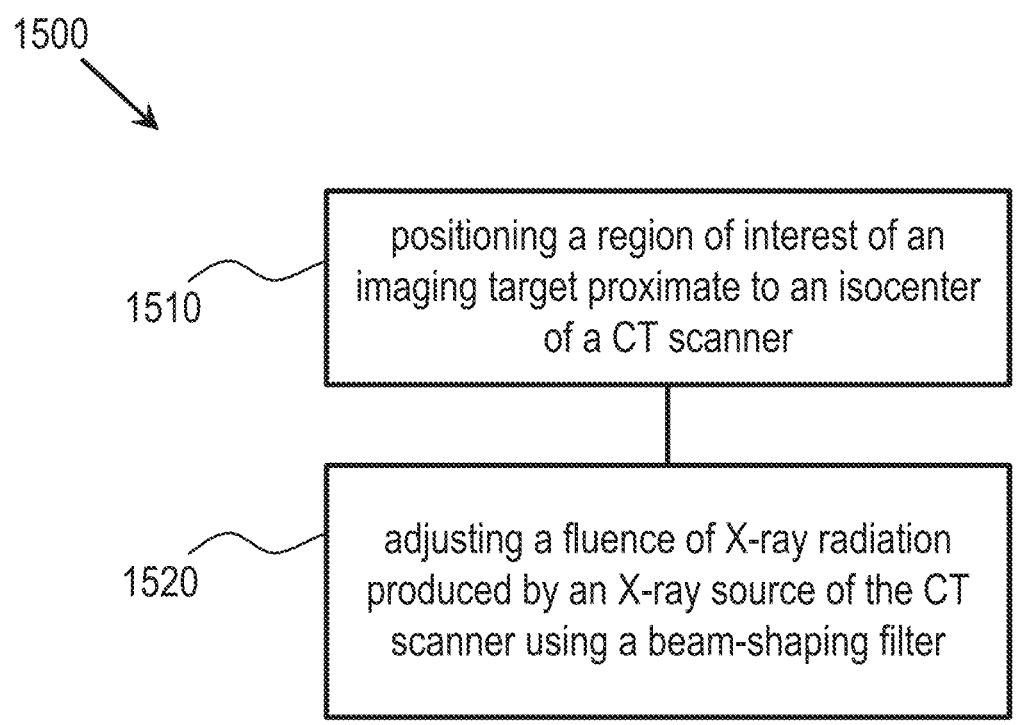
FIG. 15 illustrates steps of an example method of reducing radiation dose in computed tomography (CT) imaging according to the disclosed technology.

FIG. 15 illustrates steps of an example method 1500 of reducing radiation dose in computed tomography (CT) imaging according to the disclosed technology. Step 1510 of the method 1500 includes positioning a region of interest of an imaging target proximate to an isocenter of a CT scanner. Step 1520 of the method 1500 includes adjusting a fluence of X-ray radiation produced by an X-ray source of the CT scanner using a beam-shaping filter.

Figure 16:
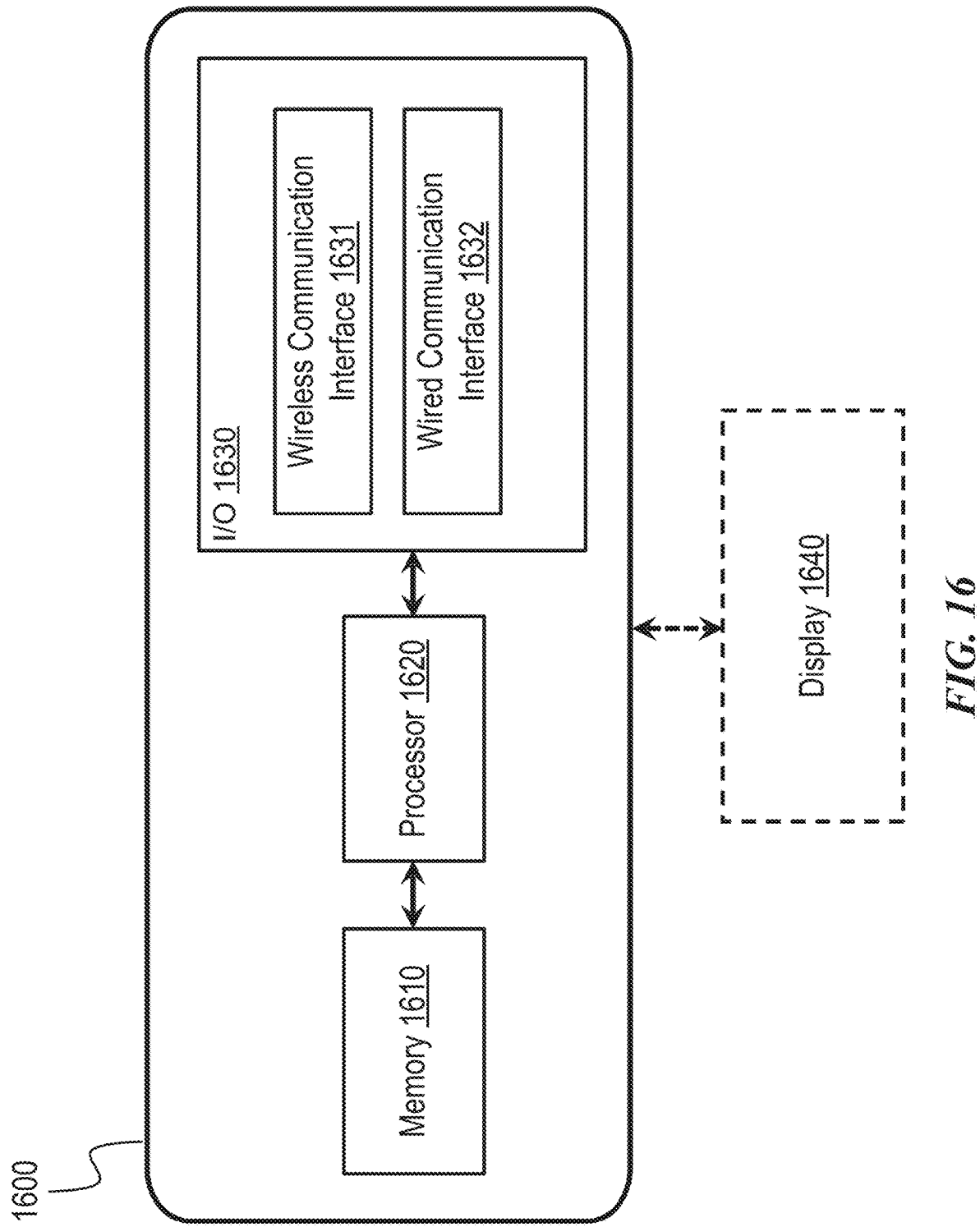
FIG. 16 shows a block diagram of an example embodiment of an electronic device according to the disclosed technology.

FIG. 16 shows a block diagram of an example embodiment of an electronic device 1600 according to the disclosed technology. In various implementations, the electronic device 1600 is operable to store and execute software applications and algorithms to process signals (e.g., CT images) obtained by the electronic device 1600 from a CT scanner (or certain elements of the CT scanner) according to the disclosed technology and implement various controls of the CT scanner, such as control of the X-ray tube current of the scanner or positioning of a region of interest of a patient at or proximate to an isocenter of the scanner, for example.

In various embodiments, the electronic device 1600 can be implemented, for example, as a portable computing device, such as a laptop or a mobile communications device, such as a smartphone, tablet or wearable device, like a smartwatch, glasses, etc.; and/or the electronic device 1600 can be implemented as a stationary computing device, such as a desktop computer. In some embodiments, the electronic device 1600 can be a part of a CT scanner.

In some embodiments, the electronic device 1600 includes a processor 1620 configured to process data, a memory 1610 in communication with the processor 1620 configured to store data, and an input/output (I/O) communication interface (or unit) 1630 configured to interface the processor 1620 and/or the memory 1610 to other elements of the electronic device 1600 as well as to various modules, units, or devices, such as external computing devices, data storage devices, or communication devices, for example.

For example, the processor 1620 can include a central processing unit (CPU) or a microcontroller unit (MCU) or a graphics processing unit (GPU). For example, the memory 1610 can include and store processor-executable code, which, when executed by the processor 1620, configures the electronic device 1600 to perform various operations, e.g., such as receiving information, commands, and/or data, processing information, commands, and/or data, and transmitting or providing information, commands, and/or data to another element of the electronic device 1600 and/or to another device external to the electronic device 1600.

In some implementations, the electronic device 1600 can transmit raw or processed data (e.g., CT images) to a computer system or a computer network which can include one or more remote computational processing devices (e.g., servers) and which can be accessible via a communication network such as the Internet (such computer systems or networks are sometimes referred to as being located "in the cloud").

To support various functions of the electronic device 1600, the memory 1610 can store information and data, such as instructions, software, values, voltage or current profiles, and other data processed or referenced by the processor 1620. For example, various types of Random Access Memory (RAM) devices, Read Only Memory (ROM) devices, Flash Memory devices, and other suitable storage media can be used to implement storage functions of the memory 1610.

In some embodiments, the I/O unit 1630 includes a wireless communication interface 1631, such as a wireless transmitter configured to transmit stored and/or processed data, for example, or a wireless transceiver (Tx/Rx) configured to transmit and receive data. For example, in some embodiments, the I/O unit 1630 can also include a wired communication interface 1632, which can be used to exchange electric signals between elements of the electronic device 1600 as well as between the electronic device 1600 and other devices. The I/O unit 1630 can utilize various types of wired or wireless interfaces compatible with typical data communication standards, for example, which can be used in communications of the electronic device 1600 including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, NFC (Near Field Communication), and parallel interfaces. In some embodiments, the electronic device 1600 uses its I/O unit 1630 for the purpose of data transfer to another device as well as for receiving data (e.g., current profiles for the X-ray tube of the CT scanner or coordinates (e.g., 3D or 2D) of a region of interest of an imaging target) from another device.

In some embodiments, the electronic device 1600 includes or is otherwise interfaced with a display unit 1640, which can include a visual display such as a display screen, an audio display such as a speaker, or any other type of display or combinations thereof.

The I/O unit 1630 of the electronic device 1600 can also interface with other external interfaces, sources of data, data storage devices, and/or visual or audio display devices, etc. to retrieve and transfer data and information that can be processed by the processor 1620, stored in the memory 1610, or exhibited on an output unit (e.g., the display unit 1640) of the electronic device 1600 or an external device. For example, the display unit 1640 can be configured to be in data communication with the electronic device 1600, e.g., via the I/O unit 1630, to provide a visual display, an audio display, and/or other sensory display that produces the user interface of a software application. In some examples, the display unit 1640 can include various types of screen displays, speakers, or printing interfaces, e.g., including but not limited to, light emitting diode (LED), liquid crystal display (LCD) monitor or screen, cathode ray tube (CRT) as a visual display; audio signal transducer apparatuses as an audio display, etc.

Figure 17:
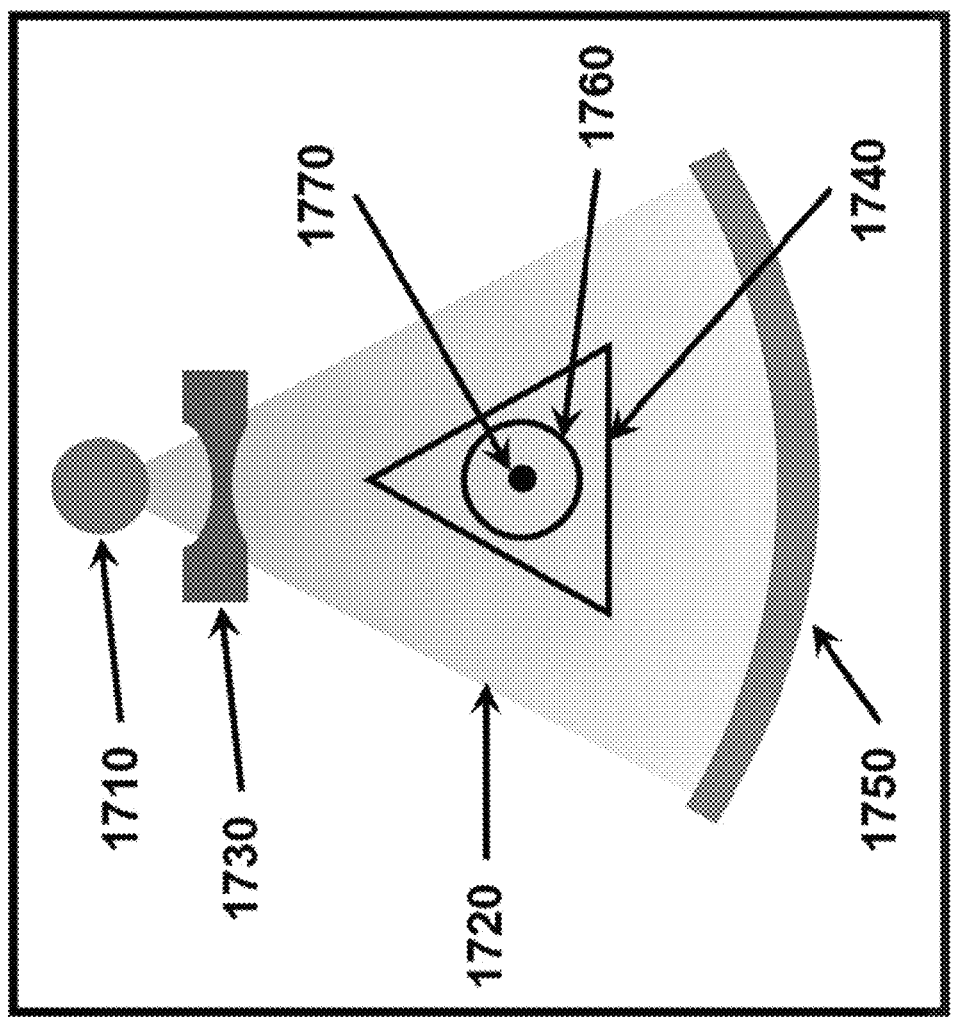
FIG. 17 shows a schematic illustration of a CT scanner according to the disclosed technology.

FIG. 17 shows a schematic illustration of a CT scanner 1700 according to the disclosed technology. The CT scanner 1700 includes an X-ray source 1710 that is configured to generate X-ray beams 1720 (e.g., in a fan configuration). The X-ray beams 1720 pass through a beam-shaping filter 1730 and further pass through an imaging target 1740 before they reach an array of detectors 1750. The beam-shaping filter 1730 of the scanner 1700 is disposed between the X-ray source 1710 of the scanner and a location where a region of interest 1760 of the imaging target 1740 is placed. The CT scanner 1700 is configured such that an isocenter 1770 of the scanner is proximate to the region of interest 1760 of the imaging target 1740 (e.g., the isocenter 1770 is within the region of interest 1760). In some implementations, the CT scanner 1700 is configured to position the isocenter 1770 of the scanner proximate to the region of interest 1760 of the imaging target 1740 (e.g., such that the isocenter 1770 is within the region of interest 1760 or such that the isocenter 1770 is at a center of the region of interest 1760). The CT scanner 1700 is further configured to adjust a fluence of X-ray radiation produced by the X-ray source 1710 using the beam-shaping filter 1730, wherein the beam-shaping filter 1730 is configured to attenuate the X-ray radiation on areas of the imaging target located outside of the region of interest and, at the same time, transmit the X-ray radiation to the areas of the imaging target located outside of the region of interest to provide a fluence of the X-ray radiation on the areas of the imaging target located outside of the region of interest at a level less than a predetermined fraction of a fluence of the X-ray radiation within the region of interest (or on the region of interest; or at a level that is greater than a predetermined fluence value).

Figure 18:
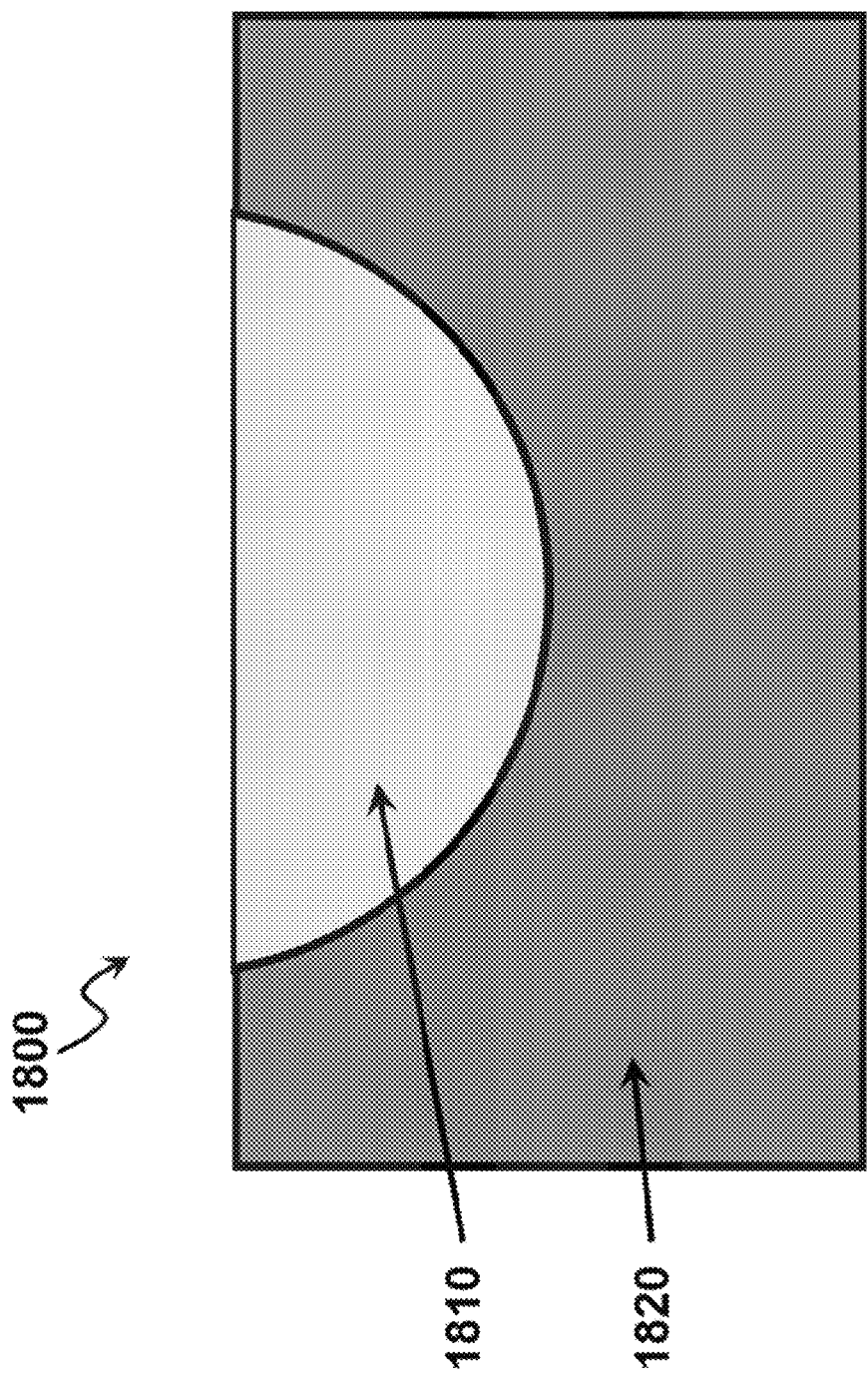
FIG. 18 illustrates a cross-section of a beam-shaping filter according to an example embodiment of the disclosed technology.

FIG. 18 illustrates a cross-section of a beam-shaping filter 1800 according to an example embodiment of the disclosed technology. As shown in FIG. 18, the filter 1800 can include a part of its body, 1810, that can be tailored (e.g., in its shape and/or material properties) to a region of interest of an imaging target. The part 1810 of the filter 1800 can be either fully transparent for X-rays produced by an X-ray source of a CT scanner or, in certain implementations, the part 1810 of the filter 1800 can be structured to attenuate the X-rays to a certain level (e.g., to 80% of the intensity of the X-ray source). X-rays emitted by the X-ray source of the CT scanner that pass through the part 1810 of the filter 1800 impinge on the region of interest of an imaging target. FIG. 18 also illustrates that the filter 1800 includes a part 1820 which is configured to attenuate X-rays produced by the X-ray source of the CT scanner. X-rays emitted by the X-ray source of the CT scanner that pass through the part 1820 of the filter 1800 impinge on the areas of the imaging target outside of its region of interest. Any of the parts 1810 or 1820 of the filter 1800 can be manufactured in such a way as to provide a varying thickness of the material across the part in order to tune the degree of attenuation of X-ray radiation by different areas of the part as well as to shape the energy spectrum of the photons emitted by the X-ray source. Also, any of the parts 1810 or 1820 of the filter 1800 can be manufactured using different materials (e.g., dense materials which absorb X-ray photons such as plastics (e.g., Teflon) or metals (e.g., aluminum, titanium, etc.)).

An aspect of the disclosed technology relates to a method of reducing radiation dose in computed tomography (CT) imaging, comprising: positioning a region of interest of an imaging target proximate to an isocenter of a CT scanner (according to some example embodiments, the method includes positioning a CT scanner or an element of the CT scanner (such as, e.g., a table or a platform on which a patient is typically placed within the scanner) such that an isocenter of the CT scanner is proximate to a region of interest of an imaging target); and adjusting a fluence of X-ray radiation produced by an X-ray source of the CT scanner using a beam-shaping filter, wherein the beam-shaping filter is disposed between the X-ray source of the CT scanner and the region of interest, and wherein the beam-shaping filter is configured to attenuate the X-ray radiation on areas of the imaging target located outside of the region of interest and simultaneously transmit the X-ray radiation to the areas of the imaging target located outside of the region of interest to provide a fluence of the X-ray radiation on the areas of the imaging target located outside of the region of interest at a level less than a predetermined fraction of a fluence of the X-ray radiation within the region of interest (or, in some example embodiments, at a level that is greater than a predetermined fluence value).

In some example embodiments of the method of reducing radiation dose in computed tomography (CT) imaging, the positioning the region of interest of the imaging target is such that the isocenter of the CT scanner is within the region of interest. In certain example embodiments, the isocenter of the CT scanner is co-located with a center of the region of interest. In some example embodiments, the isocenter of the CT scanner is at the center of the region of interest. According to some example embodiments, the beam-shaping filter is a static filter. In certain example embodiments, the beam-shaping filter has a fixed geometry. In some example embodiments, the beam-shaping filter has a variable (or adjustable or changeable) geometry (e.g., a size or a shape of the filter or of any part or element (e.g., an opening or an orifice) of the filter). According to some example embodiments, the beam-shaping filter is configured to attenuate (or modulate) the fluence of X-ray radiation produced by the X-ray source as a function of a distance from the isocenter (or as a function of a detector angle; or as a function of a distance from a center of an X-ray source). In certain example embodiments, the beam-shaping filter is configured to provide a first degree of fluence attenuation for the distances from the isocenter within a first range of distances and provide a second degree of fluence attenuation for the distances from the isocenter outside the first range of distances, wherein the first degree of fluence attenuation is different from the second degree of fluence attenuation. In some example embodiments, the first degree of fluence attenuation is lower than or higher than the second degree of fluence attenuation. In some example embodiments, the method further includes modulating a current of the X-ray source. According to some example embodiments, the method further includes modulating X-ray tube current. In certain example embodiments, the method also includes modulating X-ray tube current (or current of the X-ray source) as a part of an automated exposure control. According to some example embodiments, the modulation is generated based on the region of interest. In some example embodiments, the modulation is tailored to the region of interest. According to certain example embodiments, the modulation is a function of X-ray attenuation characteristics of the imaging target only for X-rays that pass through the region of interest. In some example embodiments, the modulation is a function of X-ray attenuation characteristics of the region of interest only. According to some example embodiments, the modulation function is obtained based on equalizing an average value of an inverse square root of a photon count in the region of interest over a range of view angles. According to certain example embodiments, the modulation function is obtained using equalizing a noise index in the region of interest over a range of view angles. In some example embodiments, the range of view angles includes all view angles. In some example embodiments, the modulation function is obtained using a low-dose (scout) scan over a range of view angles. In certain example embodiments, the modulation function is obtained using one or more scans of the imaging target. According to some example embodiments, geometry of the filter (e.g., a size or a shape of the filter or of any part or element (e.g, an opening or an orifice) of the filter) is selected using at least one of: age, sex, body mass index, race, or ethnicity of a person. In some example embodiments, the positioning the region of interest of the imaging target is performed based on at least one of: age, sex, body mass index, race, or ethnicity of a person. In some example embodiments, the region of interest is a heart. According to some example embodiments, the beam-shaping filter is configured to provide a fluence of the X-ray radiation on the areas of the imaging target located outside of the region of interest at a level that is greater than 0% and less than 10% of a fluence of the X-ray radiation within (or on) the region of interest. In some example embodiments, the beam-shaping filter is configured to provide a fluence of the X-ray radiation on the areas of the imaging target located outside of the region of interest at a level that is greater than 0% and less than 5% of a fluence of the X-ray radiation within the region of interest. In certain example embodiments, the beam-shaping filter is configured to provide a fluence of the X-ray radiation on the areas of the imaging target located outside of the region of interest at a level that is greater than 0% and less than 2% of a fluence of the X-ray radiation within the region of interest. According to some example embodiments, the beam-shaping filter is configured to provide a fluence of the X-ray radiation on the areas of the imaging target located outside of the region of interest at a level that is greater than 0% and less than 1% of a fluence of the X-ray radiation within the region of interest. In some example embodiments, the beam-shaping filter is configured such that an average fluence of the X-ray radiation on the areas of the imaging target located outside of the region of interest is larger than zero and at least 10 times lower compared to an average fluence of the X-ray radiation on the region of interest. In certain example embodiments, the beam-shaping filter is configured such that an average fluence of the X-ray radiation on the areas of the imaging target located outside of the region of interest is larger than zero and at least 20 times lower compared to an average fluence of the X-ray radiation on the region of interest. According to some example embodiments, the beam-shaping filter is configured such that an average fluence of the X-ray radiation on the areas of the imaging target located outside of the region of interest is larger than zero and at least 50 times lower compared to an average fluence of the X-ray radiation on the region of interest. In some example embodiments, the beam-shaping filter is configured such that an average fluence of the X-ray radiation on the areas of the imaging target located outside of the region of interest is larger than zero and at least 100 times lower compared to an average fluence of the X-ray radiation on the region of interest.

Another aspect of the disclosed technology relates to a computed tomography (CT) scanner, comprising: an X-ray source, wherein the CT scanner is configured to: position a region of interest of an imaging target proximate to an isocenter of the CT scanner; and adjust a fluence of X-ray radiation produced by the X-ray source using a beam-shaping filter disposed between the X-ray source and the region of interest, wherein the beam-shaping filter is configured to attenuate the X-ray radiation on areas of the imaging target located outside of the region of interest and, at the same time, transmit the X-ray radiation to the areas of the imaging target located outside of the region of interest to provide a fluence of the X-ray radiation on the areas of the imaging target located outside of the region of interest at a level less than a predetermined fraction of a fluence of the X-ray radiation within the region of interest (or, according to some example embodiments, at a level greater than a predetermined fluence value).

Yet another aspect of the disclosed technology relates to a computed tomography (CT) scanner, comprising: an X-ray source; and a beam-shaping filter disposed between the X-ray source and a location where a region of interest of an imaging target is placed, wherein: the CT scanner is configured such that an isocenter of the CT scanner is proximate to the region of interest, wherein the CT scanner is further configured to adjust a fluence of X-ray radiation produced by the X-ray source using the beam-shaping filter, and wherein the beam-shaping filter is configured to attenuate the X-ray radiation on areas of the imaging target located outside of the region of interest and, at the same time, transmit the X-ray radiation to the areas of the imaging target located outside of the region of interest to provide a fluence of the X-ray radiation on the areas of the imaging target located outside of the region of interest at a level less than a predetermined fraction of a fluence of the X-ray radiation within the region of interest (or, in certain example embodiments, at a level greater than a predetermined fluence value).

In some example embodiments, the scanner is configured to position the region of interest of the imaging target such that the isocenter of the scanner is within the region of interest According to some example embodiments, the scanner is configured such that the isocenter of the scanner is within the region of interest. In certain example embodiments, the beam-shaping filter is a static filter. According to some example embodiments, the beam-shaping filter is configured to attenuate the fluence of X-ray radiation produced by the X-ray source as a function of a distance from the isocenter. In some example embodiments, the beam-shaping filter is configured to provide a first degree of fluence attenuation for the distances from the isocenter within a first range of distances and provide a second degree of fluence attenuation for the distances from the isocenter outside the first range of distances, wherein the first degree of fluence attenuation is different from the second degree of fluence attenuation. According to some example embodiments, the scanner is configured to modulate a current of the X-ray source. In certain example embodiments, the scanner is configured to modulate X-ray tube current. According to some example embodiments, the modulation is a function of X-ray attenuation characteristics of the imaging target only for X-rays that pass through the region of interest. In some example embodiments, the scanner is configured to obtain the modulation function based on equalizing an average value of an inverse square root of a photon count in the region of interest over a range of view angles. In certain example embodiments, the region of interest is a heart. According to some example embodiments, the computed tomography scanner is configured to implement a method according to the technology disclosed in this patent document.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method of reducing radiation dose in computed tomography (CT) imaging, comprising:
    positioning a region of interest of an imaging target proximate to an isocenter of a CT scanner; and
    adjusting a fluence of X-ray radiation produced by an X-ray source of the CT scanner using a beam-shaping filter,
    wherein the beam-shaping filter is disposed between the X-ray source of the CT scanner and the region of interest, and
    wherein the beam-shaping filter is configured to attenuate the X-ray radiation on areas of the imaging target located outside of the region of interest and simultaneously transmit the X-ray radiation to the areas of the imaging target located outside of the region of interest to provide a fluence of the X-ray radiation on the areas of the imaging target located outside of the region of interest at a level less than a predetermined fraction of a fluence of the X-ray radiation within the region of interest, and
    wherein the beam-shaping filter has a first part including a first material and a second part including a second material different from the first material.

2. The method of claim 1, wherein the positioning the region of interest of the imaging target is such that the isocenter of the CT scanner is within the region of interest.

3. The method of claim 1, wherein the beam-shaping filter is a static filter.

4. The method of claim 3, wherein geometry of the filter is selected using at least one of: age, sex, or body mass index of a person.

5. The method of claim 1, wherein the beam-shaping filter is configured to attenuate the fluence of X-ray radiation produced by the X-ray source as a function of a distance from the isocenter.

6. The method of claim 5, wherein the beam-shaping filter is configured to provide a first degree of fluence attenuation for the distances from the isocenter within a first range of distances and provide a second degree of fluence attenuation for the distances from the isocenter outside the first range of distances, wherein the first degree of fluence attenuation is different from the second degree of fluence attenuation.

7. The method of claim 1, comprising modulating a current of the X-ray source, and wherein the modulation is generated based on the region of interest.

8. The method of claim 7, wherein the modulation is a function of X-ray attenuation characteristics of the imaging target only for X-rays that pass through the region of interest.

9. The method of claim 8, wherein the modulation is obtained based on equalizing an average value of an inverse square root of a photon count in the region of interest over a range of view angles.

10. The method of claim 1, wherein the region of interest is a heart.

11. The method of claim 1, wherein the first material has a varying thickness across the first part in order to tune the degree of attenuation of X-ray radiation across the first part and the second material has a varying thickness across the second part in order to tune the degree of attenuation of X-ray radiation across the second part.

12. A computed tomography (CT) scanner, comprising:
    an X-ray source; and
    a beam-shaping filter disposed between the X-ray source and a location where a region of interest of an imaging target is placed, wherein:
        the CT scanner is configured such that an isocenter of the CT scanner is proximate to the region of interest wherein the CT scanner is further configured to adjust a fluence of X-ray radiation produced by the X-ray source using the beam-shaping filter, and
        wherein the beam-shaping filter is configured to attenuate the X-ray radiation on areas of the imaging target located outside of the region of interest and, at the same time, transmit the X-ray radiation to the areas of the imaging target located outside of the region of interest to provide a fluence of the X-ray radiation on the areas of the imaging target located outside of the region of interest at a level less than a predetermined fraction of a fluence of the X-ray radiation within the region of interest, and
        wherein the beam-shaping filter has a first part including a first material and a second part including a second material different from the first material such that a thickness of the first part decreases from a center of the beam-shaping filter toward an edge of the beam-shaping filter.

13. The computed tomography scanner of claim 12, wherein the scanner is configured such that the isocenter of the scanner is within the region of interest, or wherein the scanner is configured to modulate a current of the X-ray source.

14. The computed tomography scanner of claim 13, wherein the modulation is a function of X-ray attenuation characteristics of the imaging target only for X-rays that pass through the region of interest.

15. The computed tomography scanner of claim 13, wherein the scanner is configured to obtain the modulation based on equalizing an average value of an inverse square root of a photon count in the region of interest over a range of view angles.

16. The computed tomography scanner of claim 12, wherein the beam-shaping filter is a static filter.

17. The computed tomography scanner of claim 12, wherein the beam-shaping filter is configured to attenuate the fluence of X-ray radiation produced by the X-ray source as a function of a distance from the isocenter.

18. The computed tomography scanner of claim 17, wherein the beam-shaping filter is configured to provide a first degree of fluence attenuation for the distances from the isocenter within a first range of distances and provide a second degree of fluence attenuation for the distances from the isocenter outside the first range of distances, wherein the first degree of fluence attenuation is different from the second degree of fluence attenuation.

19. The computed tomography scanner of claim 12, wherein the region of interest is a heart.

20. The computed tomography scanner of claim 12, wherein the first material has a varying thickness across the first part in order to tune the degree of attenuation of X-ray radiation across the first part and the second material has a varying thickness across the second part in order to tune the degree of attenuation of X-ray radiation across the second part.

* * * * *